US008861817B2

(12) United States Patent
Imamura et al.

(10) Patent No.: US 8,861,817 B2
(45) Date of Patent: Oct. 14, 2014

(54) IMAGE PROCESSING APPARATUS, CONTROL METHOD THEREOF, AND COMPUTER PROGRAM

(75) Inventors: Hiroshi Imamura, Tokyo (JP); Akihiro Katayama, Zama (JP)

(73) Assignee: Canon Kabushiki Kaisha, Tokyo (JP)

( * ) Notice: Subject to any disclaimer, the term of this patent is extended or adjusted under 35 U.S.C. 154(b) by 338 days.

(21) Appl. No.: 13/318,848

(22) PCT Filed: May 26, 2010

(86) PCT No.: PCT/JP2010/059302
§ 371 (c)(1), (2), (4) Date: Nov. 4, 2011

(87) PCT Pub. No.: WO2010/140601
PCT Pub. Date: Dec. 9, 2010

(65) Prior Publication Data
US 2012/0063660 A1   Mar. 15, 2012

(30) Foreign Application Priority Data

Jun. 2, 2009   (JP) .................................. 2009-133455

(51) Int. Cl.
*G06T 5/00* (2006.01)
*A61B 3/00* (2006.01)
*A61B 3/13* (2006.01)
*A61B 8/10* (2006.01)

(52) U.S. Cl.
USPC ............ 382/128; 382/131; 382/274; 351/206

(58) Field of Classification Search
None
See application file for complete search history.

(56) References Cited

U.S. PATENT DOCUMENTS

| 7,744,221 B2 * | 6/2010 | Wei et al. ...................... 351/246 |
| 7,905,596 B2 | 3/2011 | Aoki et al. |
| 2007/0285619 A1 | 12/2007 | Aoki et al. |
| 2008/0204655 A1 * | 8/2008 | Kikawa et al. ................ 351/206 |
| 2011/0134392 A1 | 6/2011 | Iwase et al. |
| 2011/0137157 A1 | 6/2011 | Imamura et al. |
| 2011/0234785 A1 | 9/2011 | Wanda et al. |

(Continued)

FOREIGN PATENT DOCUMENTS

| EP | 1 864 608 A1 | 12/2007 |
| JP | 2002-028134 A | 1/2002 |

(Continued)

OTHER PUBLICATIONS

Bagci et al. "A Method for Detection of Retinal Layers by Optical Coherence Tomography Image Segmentation." Life Science Systems and Applications Workshop, Nov. 8, 2007, pp. 144-147.*
Fuller et al. "Segmentation of Three-Dimensional Retinal Image Data." IEEE Transactions on Visualization and Computer Graphics, vol. 13, No. 6, Nov. 2007, pp. 1719-1726.*

(Continued)

*Primary Examiner* — Jon Chang
(74) *Attorney, Agent, or Firm* — Fitzpatrick, Cella, Harper & Scinto

(57) ABSTRACT

The present invention an image processing apparatus, which processes an image of a tomogram obtained by capturing an image of an eye to be examined by a tomography apparatus, comprises, layer candidate detection means for detecting layer candidates of a retina of the eye to be examined from the tomogram, artifact region determination means for determining an artifact region in the tomogram based on image features obtained using the layer candidates, and image correction means for correcting intensities in the artifact region based on a determination result of the artifact region determination means and image features in the region.

26 Claims, 31 Drawing Sheets

(56) References Cited

U.S. PATENT DOCUMENTS

| | | |
|---|---|---|
| 2012/0057127 A1 | 3/2012 | Iwase et al. |
| 2012/0130270 A1 | 5/2012 | Imamura et al. |
| 2012/0194782 A1 | 8/2012 | Imamura |

FOREIGN PATENT DOCUMENTS

| | | |
|---|---|---|
| JP | 2007-127425 A | 5/2007 |
| JP | 2007-325831 A | 12/2007 |
| JP | 2008-73099 A | 4/2008 |
| JP | 2009-78088 A | 4/2009 |
| JP | 2009-089792 A | 4/2009 |
| WO | 2004/098396 A2 | 11/2004 |

OTHER PUBLICATIONS

Zhu et al. "Layer Structures Localization in Optical Coherence Tomography Images." Symposium on Biophotonics, Nanophotonics and Metamaterials, Oct. 16, 2006, pp. 50-53.*

Sep. 27, 2013 Chinese Official Action in Chinese Patent Appln. No. 201080024458.0.

International Search Report and Written Opinion of the International Searching Authority mailed Jul. 13, 2010, in International Application No. PCT/JP2010/059302.

Delia Cabrera Fernandez, et al., "Automated detection of retinal layer structures on optical coherence tomography images", Optics Express, vol. 13, No. 25, Jan. 2005, pp. 10200-10216.

Aug. 20, 2014 European Search Report in European Patent Appln. No. 10783383.2.

* cited by examiner

IMAGE PROCESSING APPARATUS, CONTROL METHOD THEREOF, AND COMPUTER PROGRAM

TECHNICAL FIELD

The present invention relates to an image processing apparatus, control method thereof, and computer program.

BACKGROUND ART

Ophthalmic examinations are prevalently made for the purpose of earlier diagnoses of various diseases that are among the top reasons of lifestyle-related diseases and causes of blindness. A tomography apparatus for an eye portion such as an OCT (Optical Coherence Tomography) is expected to effectively give more adequate diagnoses of diseases since it allows to three-dimensionally observe the state of the interior of retina layers. By measuring a change in layer thickness of, for example, a nerve fiber layer or retina, and a change in layer geometry such as an unevenness of a retinal pigment epithelium from this tomogram, it is possible to quantitatively diagnose the degrees of progress of diseases such as glaucoma, macular edema, and age-related macular degeneration, and recovery levels after medical treatments. In order to quantitatively measure the thickness of these layers, a technique for detecting respective layers of a retina from a tomogram using a computer and measuring the thickness of these layers has been proposed (see Japanese Patent Laid-Open No. 2008-073099).

On the other hand, in an OCT tomogram, when measurement light is strongly reflected or absorbed by an object, an artifact caused by attenuation or omission of signals is often generated behind the object. Note that the object includes, for example, tissue such as a blood vessel and morbid portions such as an exudate and bleeding. As shown in FIG. 1A, when intensities are displayed normally in association with a depth direction (to be referred to as a z-axis direction or an A-scan direction hereinafter) of a retina, a maximum intensity appears in the vicinity of a retinal pigment epithelium 2. However, as shown in FIG. 1B, when an artifact region 5 is generated on the positive direction side of the z-axis of a retina blood vessel 4, intensities near a retinal pigment epithelium 6 in the artifact region 5 are attenuated or omitted. Therefore, it often becomes difficult to extract a layer and to measure the layer thickness and layer geometry depending on the degree of attenuation of intensities of the layer in the region where an artifact is generated. To solve this problem, a technique which extracts a blood vessel region from a surface image of an eye fundus, back-projects the blood vessel region onto an OCT tomogram, and interpolates layers in the vicinity of the back-projection region, so as to estimate a layer position in an artifact region caused by a blood vessel has been proposed (see Japanese Patent Laid-Open No. 2007-325831).

SUMMARY OF INVENTION

However, the technique described in Japanese Patent Laid-Open No. 2008-073099 does not disclose any method to calculate the layer position in a region where an artifact is generated.

Also, the technique described in Japanese Patent Laid-Open No. 2007-325831 simply interpolates layers near a region back-projected onto a tomogram as a region where an artifact is more likely to be generated, but it does not calculate an original layer position by detecting intensity signals of a layer attenuated in the back-projected region. Furthermore, even when image correction is executed for the purpose of layer detection, since an artifact region and other regions have different natures about intensities such as histograms and contrast levels, the artifact region is required to be determined to adaptively apply image correction.

Hence, the present invention determines a region where intensities are attenuated due to the influence of tissue such as a blood vessel or a morbid portion such as an exudate or bleeding, and applies image correction to facilitate detection of layers in that region.

One aspect of embodiments of the present invention relates to an image processing apparatus, which processes an image of a tomogram obtained by capturing an image of an eye to be examined by a tomography apparatus, comprising, layer candidate detection means for detecting layer candidates of a retina of the eye to be examined from the tomogram, artifact region determination means for determining an artifact region in the tomogram based on image features obtained using the layer candidates, and image correction means for correcting intensities in the artifact region based on a determination result of the artifact region determination means and image features in the region.

Another aspect of embodiments of the present invention relates to an image processing apparatus, which processes an image of a tomogram obtained by capturing an image of an eye to be examined by a tomography apparatus, comprising, layer candidate detection means for detecting layer candidates of a retina of the eye to be examined from the tomogram, artifact region determination means for determining an artifact region in the tomogram based on image features obtained using the layer candidates, and layer decision means for deciding a position of a layer of the retina in the artifact region, based on a determination result of the artifact region determination means, wherein the layer decision means uses a geometric model which is used to specify a layer geometry included in the artifact region and is defined by a plurality of control points, and decides the position of the layer based on evaluation functions associated with a geometry of the geometric model and evaluation functions associated with intensities near the control points.

Further features of the present invention will become apparent from the following description of exemplary embodiments (with reference to the attached drawings).

DESCRIPTION OF EMBODIMENTS

Preferred embodiments of an image processing apparatus and method according to the present invention will be described in detail hereinafter with reference to the accompanying drawings. However, the scope of the invention is not limited to illustrated examples.

First Embodiment

When an image of an eye to examined (an eye as an examination target) is to be captured by an OCT apparatus, if a blood vessel or exudate exists on a retina, since the intensity of measurement light lowers, a retinal pigment epithelium is attenuated on the obtained image, and it is difficult to detect the layer. Hence, in this embodiment, an artifact region is determined from a tomogram of an eye to be examined, and image correction is applied to that region according to a statistical amount in the region.

Figure 2:
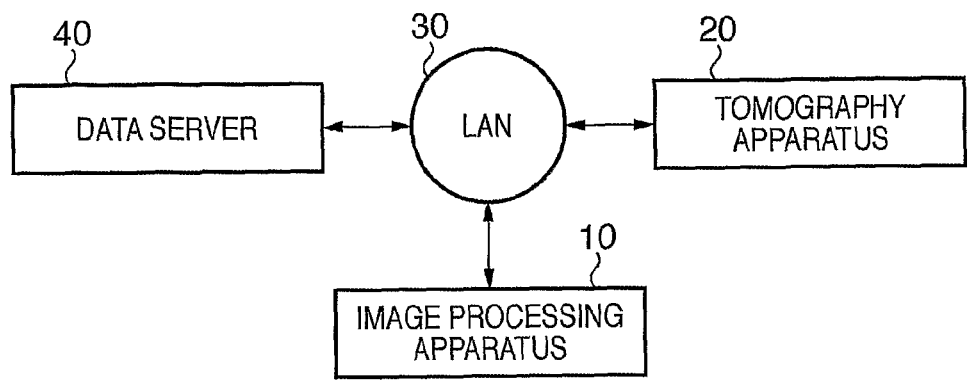
FIG. 2 is a block diagram showing the arrangement of apparatus connected to an image processing apparatus 10 according to the first embodiment.

FIG. 2 is a block diagram showing the arrangement of apparatus connected to an image processing apparatus 10 according to this embodiment. As shown in FIG. 2, the image processing apparatus 10 is connected to a tomography apparatus 20 via an optical fiber and an interface of, for example, USB or IEEE1394. The tomography apparatus 20 is connected to a data server 40 via a local area network (LAN) 30 based on, for example, Ethernet®. Note that the image processing apparatus 10 may be connected to these apparatus via an external network such as the Internet. The tomography apparatus 20 obtains a tomogram of an eye portion, and includes, for example, a time domain OCT or Fourier domain OCT. The tomography apparatus 20 three-dimensionally captures a tomogram of an eye to be examined (not shown) in response to an operation by an operator (not shown). The apparatus 20 transmits the obtained tomogram to the image processing apparatus 10. The data server 40 holds tomograms, image feature amounts, and the like of an eye to be examined. The data server 40 stores tomograms of an eye to be examined output from the tomography apparatus 20 and analysis results output from the image processing apparatus 10. The data server 40 transmits previous data associated with an eye to be examined to the image processing apparatus 10 in response to a request from the image processing apparatus 10.

Note that this embodiment will explain a case in which retinal pigment epithelium candidates are to be acquired. However, a candidate to be acquired is not limited to an outer boundary 2 of the retinal pigment epithelium. Another layer boundary (an inner boundary (not shown) of the retinal pigment epithelium, a boundary 3 between inner and outer photoreceptor segments, or an outer limiting membrane (not shown)) may be detected. When acquisition of layer candidates, determination of an artifact region, and image correction are made for an optic papilla in place of a macula portion, a region where no layer exists such as a papilla central portion (recessed portion) can be excluded in advance from a region to be processed using a known portion recognition method.

Figure 3:
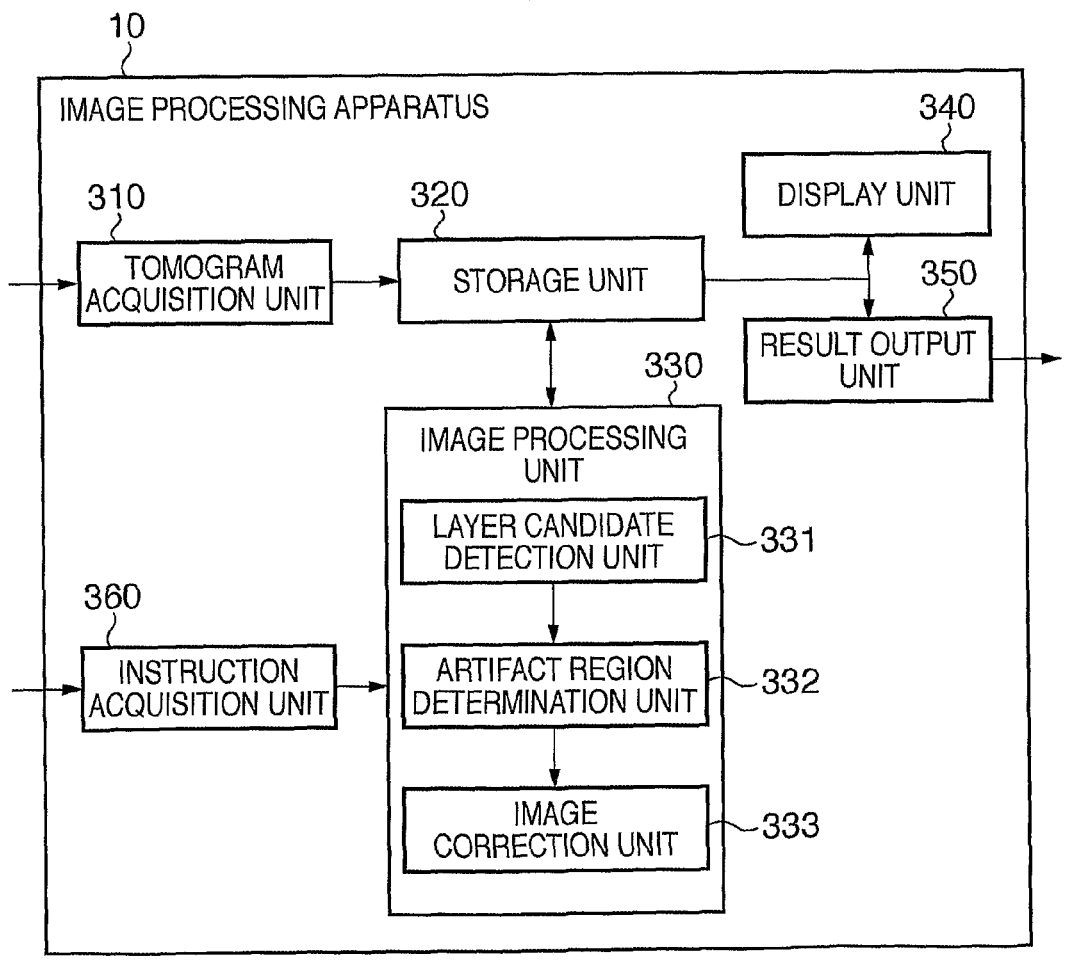
FIG. 3 is a block diagram showing the functional arrangement of the image processing apparatus 10 according to the first embodiment.
Figure 4:
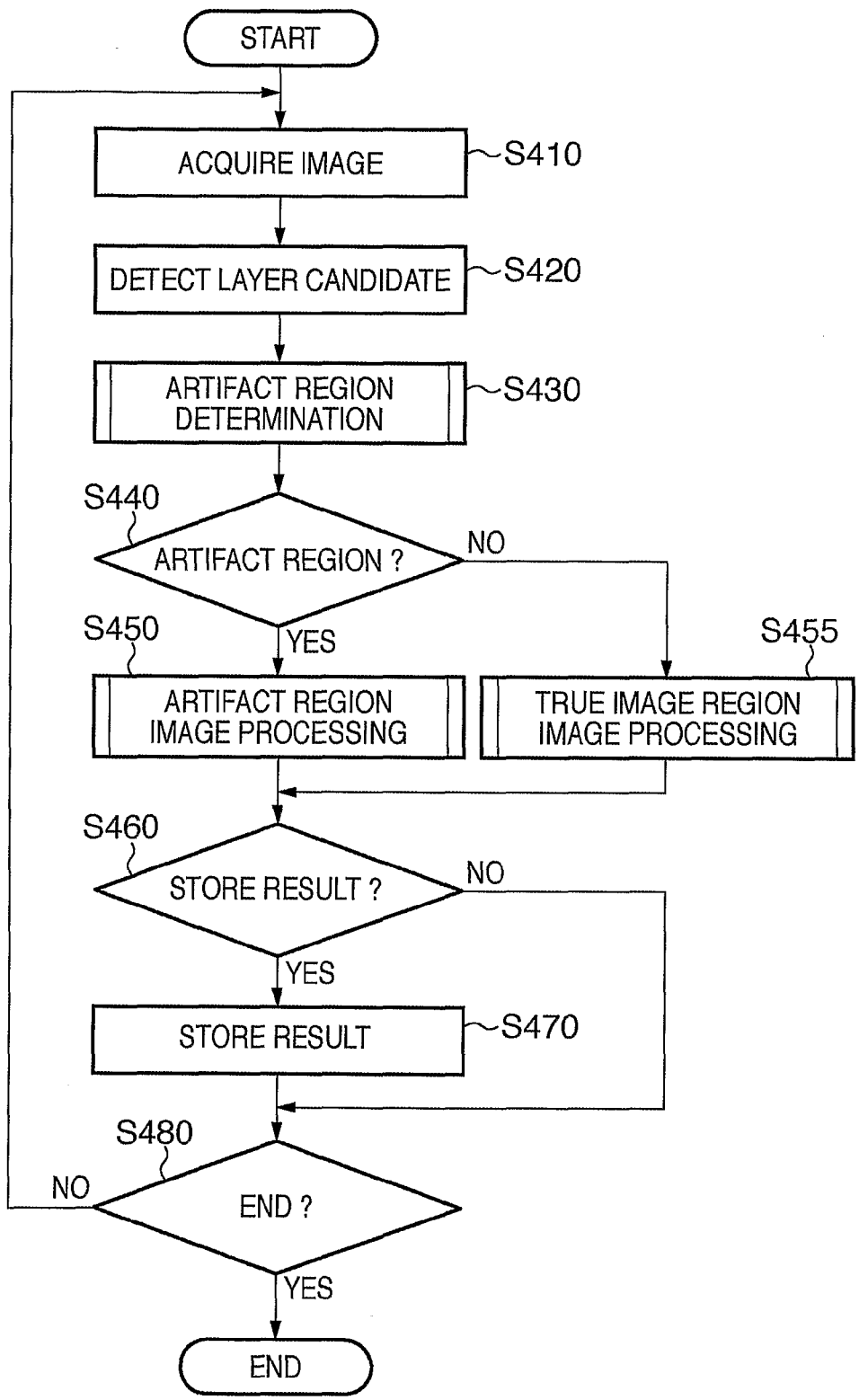
FIG. 4 is a flowchart showing the processing sequence of the image processing apparatus 10 according to the first embodiment.

The functional arrangement of the image processing apparatus 10 according to this embodiment will be described below with reference to FIG. 3. FIG. 3 is a functional block diagram of the image processing apparatus 10. As shown in FIG. 3, the image processing apparatus 10 includes a tomogram acquisition unit 310, storage unit 320, image processing unit 330, display unit 340, result output unit 350, and instruction acquisition unit 360. Furthermore, the image processing unit 330 includes a layer candidate detection unit 331, artifact region determination unit 332, and image correction unit 333. The functions of the respective blocks, which configure the image processing apparatus 10, will be described below with reference to the flowchart shown in FIG. 4 in association with the practical processing sequence executed by the image processing apparatus 10 of this embodiment.

In step S410, the tomogram acquisition unit 310 requests the tomography apparatus 20 to transmit a tomogram, and acquires a tomogram transmitted from the tomography apparatus 20. Then, the unit 310 transmits the acquired information to the storage unit 320. The storage unit 320 stores the tomogram. In step S420, the layer candidate detection unit 331 acquires the tomogram from the storage unit 320, and detects an inner limiting membrane 1 and retinal pigment epithelium candidate point sequence $\{P_i\}$ from the tomogram. The unit 331 then outputs these results to the storage unit 320.

Since retina layers have different intensities for respective layers, a contrast (edge) of density values is generated at a boundary between two neighboring layers. Hence, a layer boundary is extracted by focusing attention on this contrast. Various methods of extracting a region including such contrast are available. For example, a contrast is considered as an edge, and a layer position can be extracted by detecting the edge. More specifically, edge components are detected by applying an edge detection filter to a tomogram, and edges are searched from the vitreum side in the depth direction of an eye fundus. Then, a first peak position is detected as a boundary between the vitreum and retina layers, and a maximum peak position is detected as a retinal pigment epithelium boundary.

A layer boundary may be detected by applying a Deformable Model such as Snakes or a level set method. In case of the level set method, a level set function higher by one dimension than dimensions of a region to be detected is defined, and a layer boundary to be detected is considered as a zero level line. A contour is controlled by updating the level set function, thus detecting a layer boundary. In addition, a layer boundary may be detected using a graph theorem such as GraphCut. In this case, nodes corresponding to respective pixels of an image and terminals called a sink and source are set, and edges which couple between nodes (n-link) and those which couple between terminals (t-link) are set. A layer boundary is detected by calculating a minimum cut based on a graph which is created by giving weights to these edges.

The aforementioned layer position extraction methods may be three-dimensionally applied to a whole three-dimensional (3D) tomogram as an object to be processed, or may be independently applied to each two-dimensional (2D) tomogram while considering an input 3D tomogram as a set of 2D tomograms. Note that the method of detecting a layer boundary is not limited to these methods, and any other methods may be used as long as they can detect a layer boundary from a tomogram of an eye portion.

The artifact region determination unit 332 determines in step S430 based on a continuity of the candidate point sequence $\{P_i\}$ of the retinal pigment epithelium detected in step S420 whether or not an artifact is generated near each layer candidate point (whether or not an artifact region is generated). If an artifact region is determined, the unit 332 calculates a statistical amount associated with intensities in the artifact region. Furthermore, the unit 332 outputs the determination result to the storage unit 320. The artifact region determination processing of this step will be described in detail later using the flowchart shown in FIG. 6.

In step S440, the artifact region determination unit 332 branches processes according to the determination result obtained in step S430. That is, for a layer candidate point for which it is determined that an artifact is generated, the unit 332 transmits a signal to instruct the image correction unit 333 to execute predetermined processing (the processing sequence advances to step S450). On the other hand, if the unit 332 determines a region where no artifact is generated (to be referred to as a true image region hereinafter) other than an artifact region, it transmits a signal to instruct the display unit 340 to execute predetermined processing (the processing sequence advances to step S455).

Furthermore, in step S450 the image processing unit 330 executes analysis processing when an artifact is generated near candidate points of a predetermined layer. The processing of this step will be described in detail later using the flowchart shown in FIG. 7. On the other hand, in step S455 the display unit 340 executes normal image display processing for displaying a tomogram in association with the true image region as processing when no artifact is generated near candidate points of a predetermined layer.

In step S460, the instruction acquisition unit 360 externally acquires an instruction as to whether or not to store the current processing result associated with the eye to be examined in the data server 40. The operator inputs this instruction via, for example, a keyboard and mouse (not shown). If the operator instructs to store the current result, the process advances to step S470; otherwise, the process jumps to step S480. After that, in step S470 the result output unit 350 associates a date and time of examination, information used to identify the eye to be examined, the tomogram of the eye to be examined, and the analysis result obtained by the image processing unit 330 with each other as information to be stored, and transmits that information to the data server 40.

In step S480, the instruction acquisition unit 360 externally acquires an instruction as to whether or not to end the tomogram analysis processing by the image processing apparatus 10. The operator inputs this instruction via, for example, a keyboard and mouse (not shown). If an instruction to end the processing is acquired, the image processing apparatus 10 ends its processing. On the other hand, if an instruction to continue the processing is acquired, the process returns to step S410 to execute processing for the next eye to be examined (or re-processing for the same eye to be examined). In this manner, the processing of the image processing apparatus 10 is executed.

Figure 5:
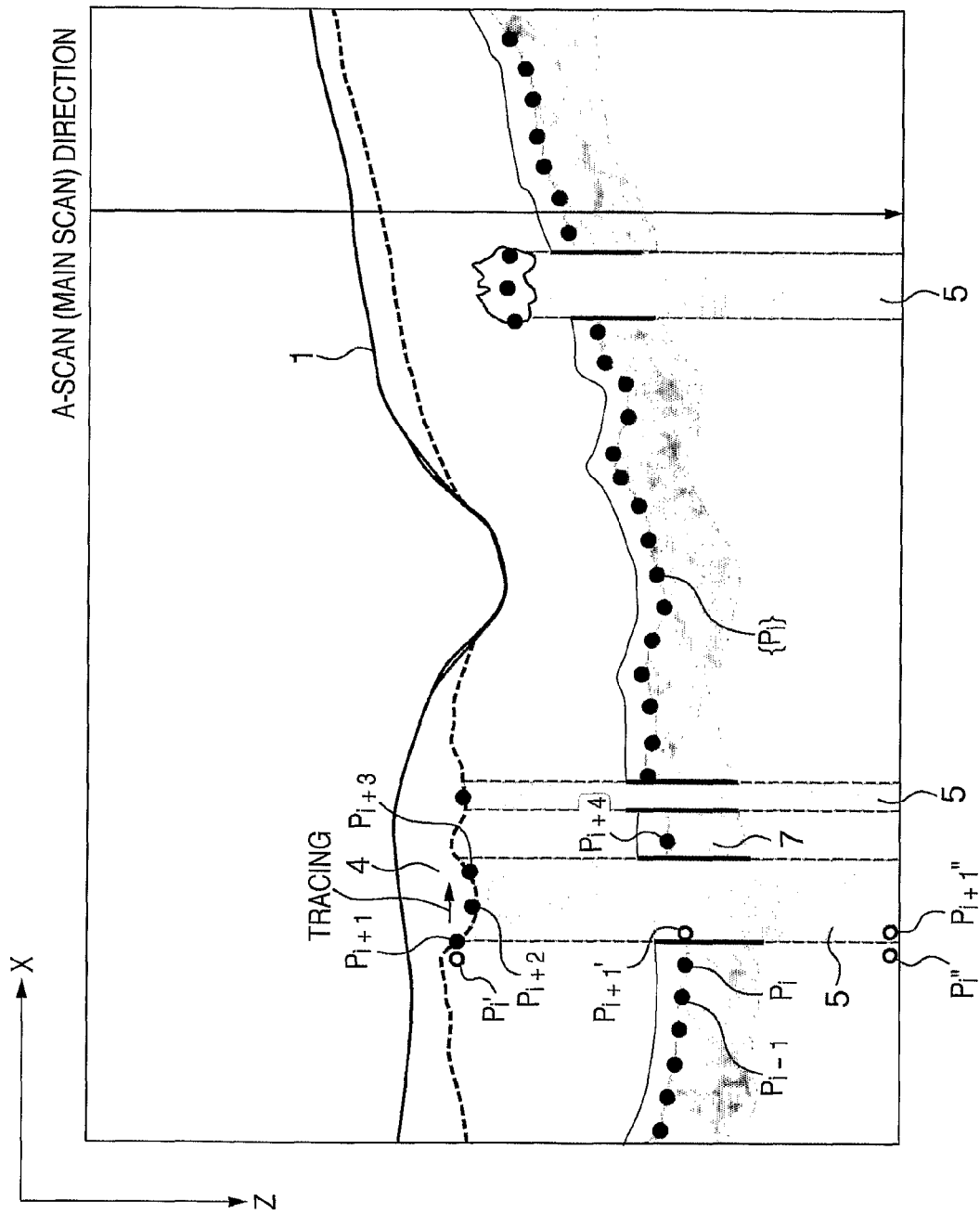
FIG. 5 is a view for explaining a determination method of an artifact region according to the first embodiment.

The sequence of the artifact region determination processing executed in step S430 will be described below using FIG. 5. FIG. 5 shows an example of a tomogram including artifact regions, and illustrates regions 5 bounded by the dotted lines as artifact regions. The following two features are known as those of such regions where artifacts are generated. Note that in the tomogram shown in FIG. 5, a longitudinal direction of the tomogram corresponding to the depth direction of a retina is defined as a z-axis, and a lateral direction perpendicular to the depth direction is defined as an x-axis. The z-axis direction corresponds to an A-scan direction.

(1) All of averages, variances, and maximum values of intensities in these regions 5 are smaller than those in true image regions.

(2) When retinal pigment epithelium candidate points are calculated in a region including these regions 5, an discontinuous portion like points $P_i$ and $P_{i+1}$ is readily generated due to erroneous extraction of a high-intensity region other than the retinal pigment epithelium, for example, a retina blood vessel region.

Thus, this embodiment determines each artifact region as follows using these features.

(i) Pairs of discontinuous layer candidate points are detected.

(ii) An artifact generation side of each pair of layer candidate points determined as discontinuous points is checked.

(iii) A layer candidate point sequence on the artifact generation side is traced until a next discontinuous point is found.

(iv) A statistical amount (average, variance, maximum value, etc.) of intensities on an A-scan line that passes through the traced layer candidate point and on the deep layer side of the layer candidate point is calculated. Note that the deep layer side indicates one, which has a larger coordinate value in the z-axis direction, of two points in FIG. 5.

(v) A region which has the discontinuous candidate point as an edge point and includes a low intensity statistical amount is determined as an artifact region. Furthermore, since the intensity statistical amount is considered as that which reflects the degree of intensity attenuation in each artifact region, it is used upon deciding an image processing method in the artifact region in step S450.

A practical method of performing artifact determination based on the candidate point sequence $\{P_i\}$ of the retinal pigment epithelium will be described below with reference to the flowchart shown in FIG. 6. In this case, a 3D tomogram as a processing target is considered as a set of 2D tomograms, and the following 2D image processing is applied to each 2D tomogram.

In step S610, a continuity C between neighboring layer candidate points is calculated for all the layer candidate points. The continuity C is given by:

$$C(P_i) = \begin{cases} 1 & (|S_i - S| \le T_s) \\ 0 & (|S_i - S| > T_s) \end{cases} \quad (1)$$

where i is a layer candidate point number, and $S_i$ is a statistical amount of intensities of pixels on a curve obtained by interpolating between layer candidate points $P_i$ and $P_{i+1}$. Also, S is a statistical amount of intensities of pixels on a curve defined by the entire layer candidate point sequence $\{P_i\}$, and $T_s$ is a threshold. In this case, as the statistical amounts $S_i$ and S of intensities, averages of intensities of pixels on the defined curves are used. In equation (1), if $|S_i - S|$ is equal to or smaller than the threshold $T_s$, it is determined that neighboring points are connected.

Figure 1A:
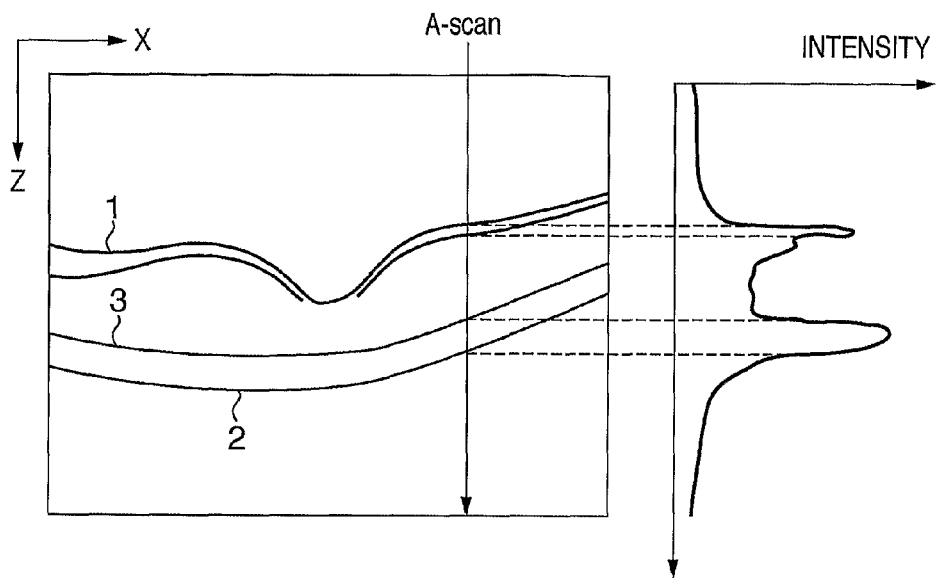
FIGS. 1A and 1B are views for explaining an example of attenuation of image signals on a retinal pigment epithelium due to the presence of a retina blood vessel.
Figure 1B:
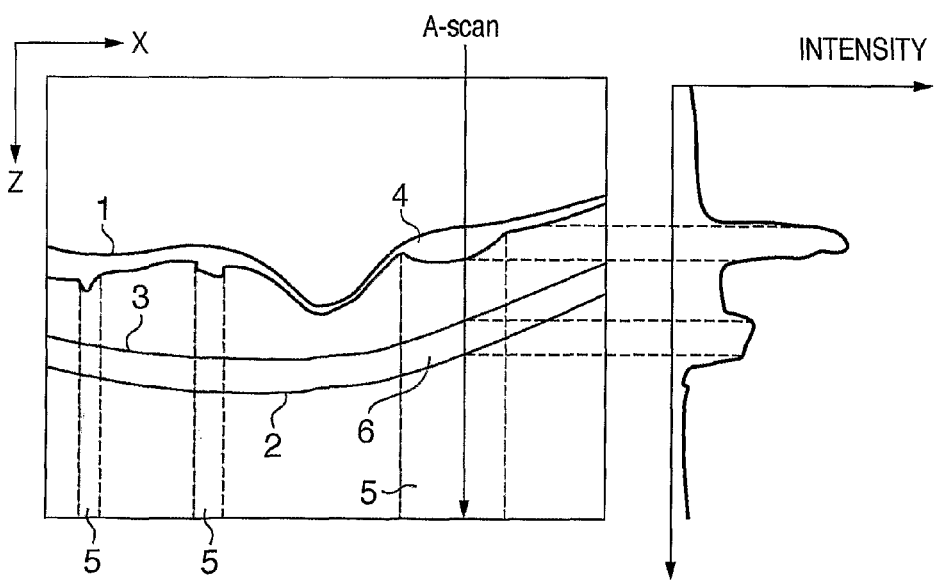

Note that the intensity statistical amount is not limited to the aforementioned amount, and other statistical amounts, for example, a maximum value, variance, mode value, and median value may be used. Alternatively, the continuity may be determined based on a combination of these statistical amounts. Also, as S, a statistical amount associated with intensities of a predetermined layer, which is calculated in advance for each image capturing apparatus or object, may be used, or a standard value, which is set in advance, may be used. Note that an index used in determination of the continuity uses the statistical amount associated with intensities on the curve, which connects the layer candidate points. However, the present invention is not limited to such specific index. For example, an edge parallel to the z-axis direction (as denoted by reference numeral 7 in FIG. 5) is generated in the vicinity of discontinuous candidate points as a result of erroneous detection of a blood vessel or exudate, and as an index that captures such feature, a degree of difference between a plurality of intensity profiles associated with the A-scan direction may be used. Note that the intensity profile indicates a graph showing the relationship between spatial positions in the A-scan direction and intensities at these positions, as indicated by the right view of FIG. 1A or 1B, and a difference between neighboring intensity profiles is normally small.

A practical calculation method of an index associated with a degree of difference between the intensity profiles is described, for example, as:

$$C(P_i) = \begin{cases} 1 & \left(\sum D > T_{d2}, \text{ for } D > T_{d1}\right) \\ 0 & \left(\sum D \le T_{d2}, \text{ for } D > T_{d1}\right) \end{cases} \quad (2)$$

(1) A difference D of intensities in the x-axis direction is calculated for pixels in a local region bounded by four points $P_i, P_{i+1}', P_i''$, and $P_{i+1}''$ shown in FIG. 5. Note that $P_i''$ is a point which has the same x-coordinate value as $P_i$, and a maximum z-coordinate value. Also, $P_{i+1}''$ is a point which has the same x-coordinate value as $P_{i+1}$, and a maximum z-coordinate value.

(2) A total value $\Sigma D$ is calculated by adding differences D equal to or larger than a threshold Td1. The value $\Sigma D$ assumes a larger value as an edge clearly appears over a broader range.

(3) When the total value $\Sigma D$ is larger than a threshold Td2, discontinuous points are determined.

The continuity may also be determined by combining the plurality of indices.

In step S620, an artifact generation side of the pair of layer candidate points determined as discontinuous points is checked to specify an edge portion of an artifact region. The artifact region edge portion specifying processing is executed for each pair of discontinuous layer candidate points. More specifically, in case of a pair of $P_i$ and $P_{i+1}$ in FIG. 5, (i) A statistical amount of intensities on the positive direction side of the z-axis of $P_i$ on an A-scan line which passes through $P_i$ is calculated.

(ii) A statistical amount of intensities on the positive direction side of the z-axis of $P_{i+1}'$ on an A-scan line which passes through $P_{i+1}$ is calculated. Note that $P_{i+1}'$ is a point which has the same x-coordinate as $P_{i+1}$, and the same z-coordinate as $P_i$.

(iii) The two statistical amounts are compared, and it is determined that an artifact is generated on the candidate point side having a smaller statistical amount. The determined candidate point having the smaller statistical amount is defined as an edge portion of an artifact region.

In this example, since the statistical amount of intensities on the $P_{i+1}$ side becomes smaller, it is determined that an artifact is generated on the $P_{i+1}$ side. Note that a method of selecting pairs of points used upon calculating the statistical amounts of intensities are not limited to the aforementioned method. For example, as shown in FIG. 5, determination may be made using $P_i'$ (a point having the same x-coordinate as $P_i$ and the same z-coordinate as $P_{i+1}$) and $P_{i+1}$.

In step S630, a layer candidate point on the artifact generation side is traced until a next discontinuous point is found to calculate a range of the artifact region. For example, a region until $P_{i+3}$ is determined as an artifact region for $P_{i+1}$ in FIG. 5.

In step S640, an average, variance, or maximum value of intensities in a region on the positive direction side of the z-axis of the respective candidate point in the region determined as the artifact region is calculated. However, a spatial range in which the statistical amount associated with intensities is calculated is not limited to such specific range. For example, an artifact region may be divided into arbitrary local regions, and the statistical amounts may be calculated for respective local regions. In this case, the layer candidate point tracing processing and calculation processing of the statistical amount associated with intensity signals need not always be executed as independent steps, and the statistical amount of intensity signals may be calculated every time layer candidate points are traced for an arbitrary range.

With the above processing, a range of the artifact region having a discontinuous portion as an end and the statistical amount of intensities in the artifact region are calculated. Note that the determination method of the artifact region is not limited to the aforementioned method. For example, artifact region determination processing may be executed not only for a B-scan image (a tomogram perpendicular to the y-axis) but also for a tomogram perpendicular to the x-axis, and an artifact region determined in both the determination processes may be determined as an artifact region. Alternatively, the determination processing may be three-dimensionally applied to a 3D tomogram.

Figure 7:
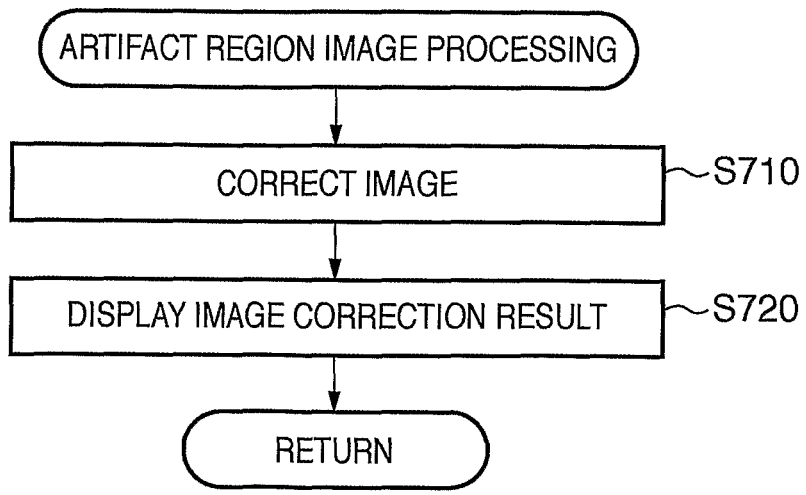
FIG. 7 is a flowchart showing the image processing sequence for a region determined as an artifact region according to the first embodiment.

The sequence of the processing executed in step S450 will be described below with reference to FIG. 7.

In step S710, the image correction unit 333 corrects intensities in each artifact region based on the statistical amount associated with the intensities in that artifact region calculated by the artifact region determination unit 332. As the intensity correction method, a method based on histogram conversion in the artifact region will be described. More specifically, the intensity average and variance in the artifact region are adjusted to be the same as those in a true image region. That is, letting x be a signal before correction, y be a signal after correction, $S_f$ and $A_f$ be a standard deviation and average value of intensities in the artifact region, respectively, and $S_t$ and $A_t$ be a standard deviation and average value of intensities in the entire image except for the artifact region, respectively, correction is applied like:

$$y=(S_t/S_f)*(x-A_f)+A_t$$

Note that the image correction method is not limited to this. For example, image correction method may be attained by methods described in (i) to (iii) below.

Alternatively, arbitrary image correction may be applied as long as it can establish a relationship of an increasing function between intensities before correction and those after correction in the artifact region.

(i) For example, intensities are linearly converted so as to make a maximum intensity in the artifact region to match that of the true image region. In this case, letting y be a intensity of the artifact region after image correction, x be a intensity of the artifact region before image correction, $I_{maxF}$ be a maximum intensity in the artifact region, a minimum intensity $I_{minF}$ in the region, and $I_{maxT}$ be a maximum intensity in the true image region, correction is applied like:

$$y=I_{maxT}*(x-I_{minF})/(I_{maxF}-I_{minF})$$

(ii) For example, edge emphasis processing such as a Sobel filter or Laplacian filter or spatial frequency filter processing that allows to pass only high-frequency components is executed.

(iii) Layer structure emphasizing filter processing based on eigenvalues of a Hessian matrix, which emphasizes a layer structure, is executed. This filter emphasizes a secondary local structure of a 3D density distribution based on the relationship among three eigenvalues ($\lambda_1, \lambda_2, \lambda_3$) of the Hessian matrix. The Hessian matrix is a square matrix made by second partial derivatives of density values I of an image, as given by:

$$H = \begin{pmatrix} I_{xx} & I_{xy} & I_{xz} \\ I_{yx} & I_{yy} & I_{yz} \\ I_{zx} & I_{zy} & I_{zz} \end{pmatrix} \qquad (3)$$

The relationship among the eigenvalues of the Hessian matrix is described by:

$$\lambda_3 \leq \lambda_2 \leq \lambda_1 \qquad (4)$$

A conditional formula for the eigenvalues required to emphasize the layer structure is described by:

$$\lambda_3 \leq \leq \lambda_2 \leq \lambda_1 = 0 \qquad (5)$$

The layer structure of a retina can be emphasized by calculating, from the three eigenvalues calculated based on these formulas:

$$S_{sheet}\{f\} = \begin{cases} |\lambda_3| \cdot \omega(\lambda_2;\lambda_3) \cdot \omega(\lambda_1;\lambda_3) & \lambda_3 < 0 \\ 0 & \text{otherwise} \end{cases} \qquad (6)$$

where $\omega(\lambda_s;\lambda_t)$ is a weighting function, which is given by:

$$\omega(\lambda_s;\lambda_t) = \begin{cases} \left(1+\frac{\lambda_s}{|\lambda_t|}\right)^\gamma & \lambda_t \leq \lambda_s \leq 0 \\ \left(1-\alpha\frac{\lambda_s}{\lambda_t}\right)^\gamma & \frac{|\lambda_t|}{\alpha} > \lambda_s > 0 \\ 0 & \text{otherwise} \end{cases} \qquad (7)$$

where $\gamma$ and $\alpha$ are weights.

Note that the aforementioned image processing methods need not always be solely executed, but they may be executed in combination. When the artifact region is divided into a plurality of local regions and statistical amounts associated with intensities are calculated for respective regions in step S640, the image correction may also be applied for respective local regions.

In step S720, the display unit 340 superimposes the correction result of the image in step S710 on the tomogram. When boundaries of each artifact region are indicated by lines, lines of a predetermined color may be used for the respective boundaries, or a layer may be presented with a translucent color without explicitly indicating boundaries. Images before and after correction may be selectively displayed for a region designated using, for example, a GUI, and information of the statistical amount associated with intensities in each artifact region calculated in step S640 may be displayed. As described above, the processing in step S450 is executed.

According to the aforementioned arrangement, the image processing apparatus 10 specifies an artifact region, and executes image correction based on, for example, a statistical amount associated with intensity in that region, thus obtaining an image from which a layer included in the artifact region can be easily detected.

Second Embodiment

In this embodiment, not only image correction is performed in an artifact region like in the first embodiment, but also a predetermined layer is detected from the corrected image. This embodiment applies image correction even to a region where an artifact is generated and intensities are attenuated, so as to facilitate detection of remaining edge information, and allows to calculate a more precise layer position by detecting that edge information.

Figure 8:
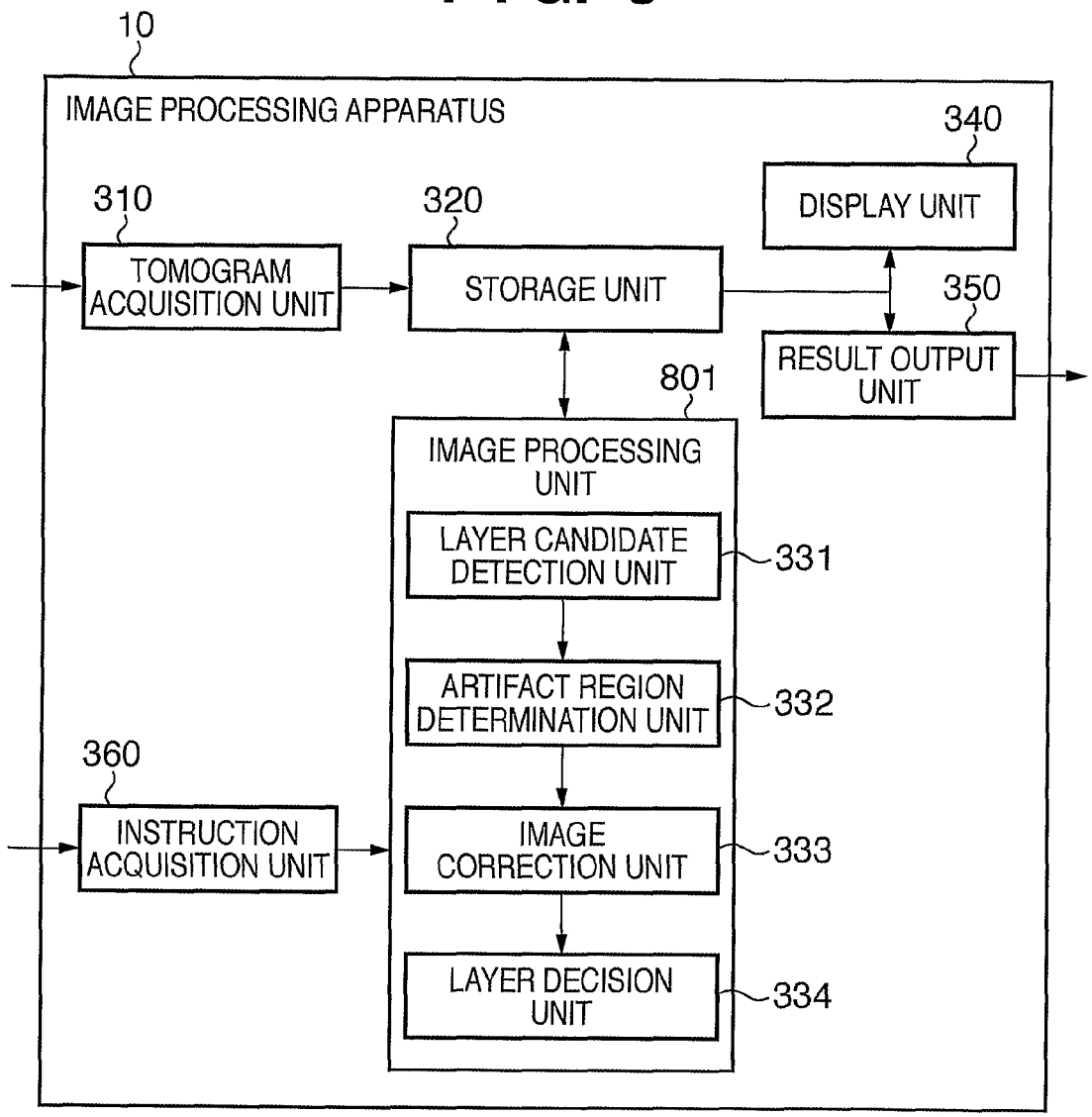
FIG. 8 is a block diagram showing the functional arrangement of an image processing apparatus 10 according to the second embodiment.

Since the arrangement of apparatus connected to an image processing apparatus 10 according to this embodiment is the same as that in the first embodiment, a description thereof will not be repeated. FIG. 8 is a functional block diagram of the image processing apparatus 10 according to this embodiment. Referring to FIG. 8, an image processing unit 801 of this embodiment is different from the arrangement of the image processing unit 330 of the image processing apparatus 10 of the first embodiment in that a layer decision unit 334 is added.

The image processing sequence of this embodiment will be described below. The processing sequence of this embodiment is the same as that shown in the flowchart of FIG. 4, except for steps S450 and S455. Hence, in this embodiment, only steps S450 and S455 will be explained, and a description of other steps will not be repeated.

In step S450, image processing in an artifact region is executed. Details of the processing of this step will be described below using FIG. 9.

In step S1010, an image correction unit 333 corrects intensities in an artifact region based on a statistical amount associated with the intensities in that region calculated by an artifact region determination unit 332. Note that this processing is the same as the image correction processing in step S710, and a detailed description thereof will not be given. In step S1020, the layer decision unit 334 acquires image features of a layer to be extracted based on intensity information of the region that has undergone the image correction by the image correction unit 333, and connects these feature points as a layer position.

For example, a retinal pigment epithelium is originally a highest-intensity region on each A-scan line, and tends to have higher intensities even in an artifact region. Thus, a layer position is decided by connecting, in an x-axis direction, pixels having maximum intensities located on the positive direction side of a z-axis of layer candidate points on respective A-scan lines of the image-corrected region. However, the method of detecting a layer from the image correction result is not limited to such specific method.

For example, a layer may be extracted by connecting pixels, which have intensities equal to or larger than a predetermined value on the positive direction side of the z-axis of layer candidate points, and have largest z-coordinates, on respective A-scan lines, in the x-axis direction. Alternatively, a layer may be extracted by calculating linear sums of intensities before and after image correction for respective pixels on respective A-scan lines of an artifact region, and connecting pixels corresponding to the maximum sum in the x-axis direction.

Alternatively, a plurality of candidate points of a retinal pigment epithelium are selected on respective A-scan lines of an artifact region, and all the layer candidate points are defined as a layer candidate point set in the artifact region. For respective combinations of layer candidate point sequences obtained from the layer candidate point set, evaluation functions associated with:

(i) a magnitude of a sum of intensities of the layer candidate point sequence; and (ii) a smoothness of the layer candidate point sequence geometry may be set, and a combination of layer candidate points, which maximizes a linear sum of the two evaluation function values, may be decided as a layer position. Note that upon selection of a combination of layer candidate points, evaluation function values may be calculated using the layer candidate point sequence which includes not only the layer candidate point sequence in the artifact region, but also layer candidate points near the region.

In step S1030, a retina layer thickness is measured by calculating distances for respective x- and y-coordinates between the calculated layer candidate point sequence corresponding to the retinal pigment epithelium, and an inner limiting membrane 1 calculated in step S420. However, the measurement contents are not limited to this. For example, an angle distribution between layer candidate points may be calculated so as to check an unevenness of a layer geometry. A layer thickness to be measured is not limited to the retina layer thickness. For example, another layer geometry such as a photoreceptor cell layer may be analyzed. Information including the calculated layer thickness and layer geometry is output to a storage unit 320.

In step S1040, a display unit 340 superimposes, on the tomogram:

(i) the layer decision result;

(ii) the layer geometry measurement result; and (iii) a range of the artifact region and the image correction result in that region.

As for (i), the display unit 340 superimposes the layer decision result in step S1020 on the tomogram. When boundaries of a layer are indicated by lines, lines of a predetermined color may be used for the respective boundaries, or a region of a layer may be presented with a translucent color without explicitly indicating boundaries. Note that upon making such display, an arrangement that allows to select a section of interest using, for example, a GUI is desirably adopted. Also, these results may be three-dimensionally displayed using a known volume rendering technique.

As for (ii), the display unit 340 displays, as the layer geometry measurement result, a distribution map of the layer thicknesses for the entire 3D tomogram (x-y plane). However, the present invention is not limited to such specific display method, and areas of respective layers in a section of interest may be displayed, or a volume of the entire predetermined layer may be displayed. Alternatively, a volume in a region designated by an operator on an x-y plane may be calculated and displayed.

As for (iii), when the reliability of the detected layer is low (for example, when signals of the detected layer are weak) in step S1020, the layer is not detected, and the image correction result is superimposed on the tomogram. However, the present invention is not limited to such specific display method of the image correction result, and the image correction result may be displayed on the display unit 340 even when the layer detection result is satisfactory.

As described above, the artifact region image processing in step S450 is executed. True image region image processing in step S455 will be described below. In step S455, as the processing in a true image region, (i) a layer candidate point sequence acquired in step S420 is defined as a layer position, and a layer geometry is measured from the layer position, and (ii) the layer position and the measurement results of the layer geometry are displayed on the display unit 340.

Hence, details of the processing of this step will be described below.

Figure 9:
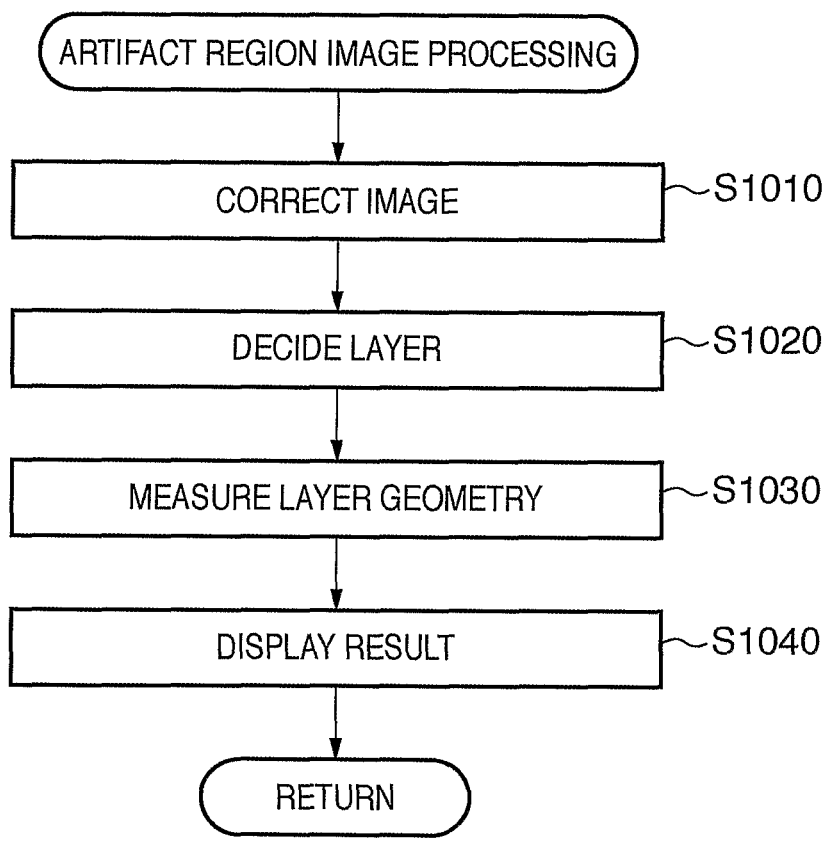
FIG. 9 is a flowchart showing the image processing sequence for a region determined as an artifact region according to the second embodiment.

The layer geometry is measured in the same manner as in step S1030 in FIG. 9. However, in case of the true image region image processing, an analysis target is a non-corrected image unlike in step S1030. Then, as in step S1040 in FIG. 10, the display unit 340 displays the result. However, in case of the true image region image processing, no image correction result is displayed unlike in step S1040.

According to the aforementioned arrangement, the image processing apparatus 10 executes image correction of a specified artifact region, and detects image features corresponding to a layer position from the correction result, thus calculating the layer position in the artifact region more precisely.

Third Embodiment

In this embodiment, in place of determination of an artifact region using only a tomogram in the first and second embodiments, a projection image is generated from a tomogram of an eye to be examined, and position information of tissue or a morbid portion extracted from the projection image is back-projected onto the tomogram, so as to narrow down artifact candidate regions in advance. In general, it is easier to calculate position information of an artifact region caused by, for example, a blood vessel (or bleeding) from a projection image than from only a tomogram. Hence, this embodiment will explain a case in which a blood vessel (bleeding) region is extracted from a projection image, that position information is mapped onto a tomogram, and an edge portion of an artifact region is searched for and specified around the mapped region, so as to calculate a range of the artifact region at higher precision.

Figure 10:
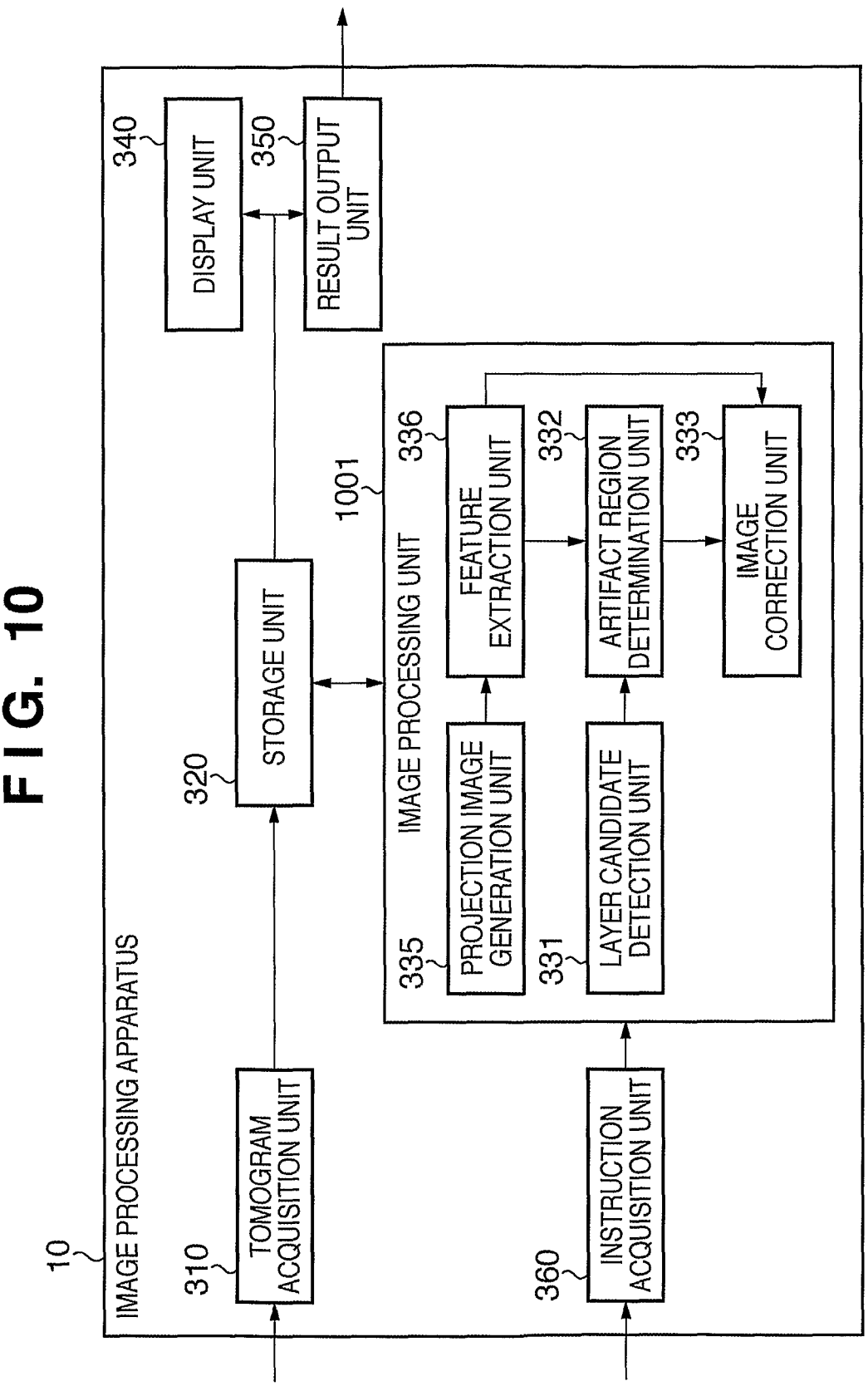
FIG. 10 is a block diagram showing the functional arrangement of an image processing apparatus 10 according to the third embodiment.

Since the arrangement of apparatus connected to an image processing apparatus 10 according to this embodiment is the same as that in the first embodiment, a description thereof will not be repeated. FIG. 10 is a functional block diagram of the image processing apparatus 10 according to this embodiment. Referring to FIG. 10, an image processing unit 1001 includes a projection image generation unit 335 and feature extraction unit 336 unlike in the image processing unit 330 of the image processing apparatus 10 of the first embodiment. Since the remaining units are the same as those in FIG. 3, a description thereof will not be repeated.

Figure 11:
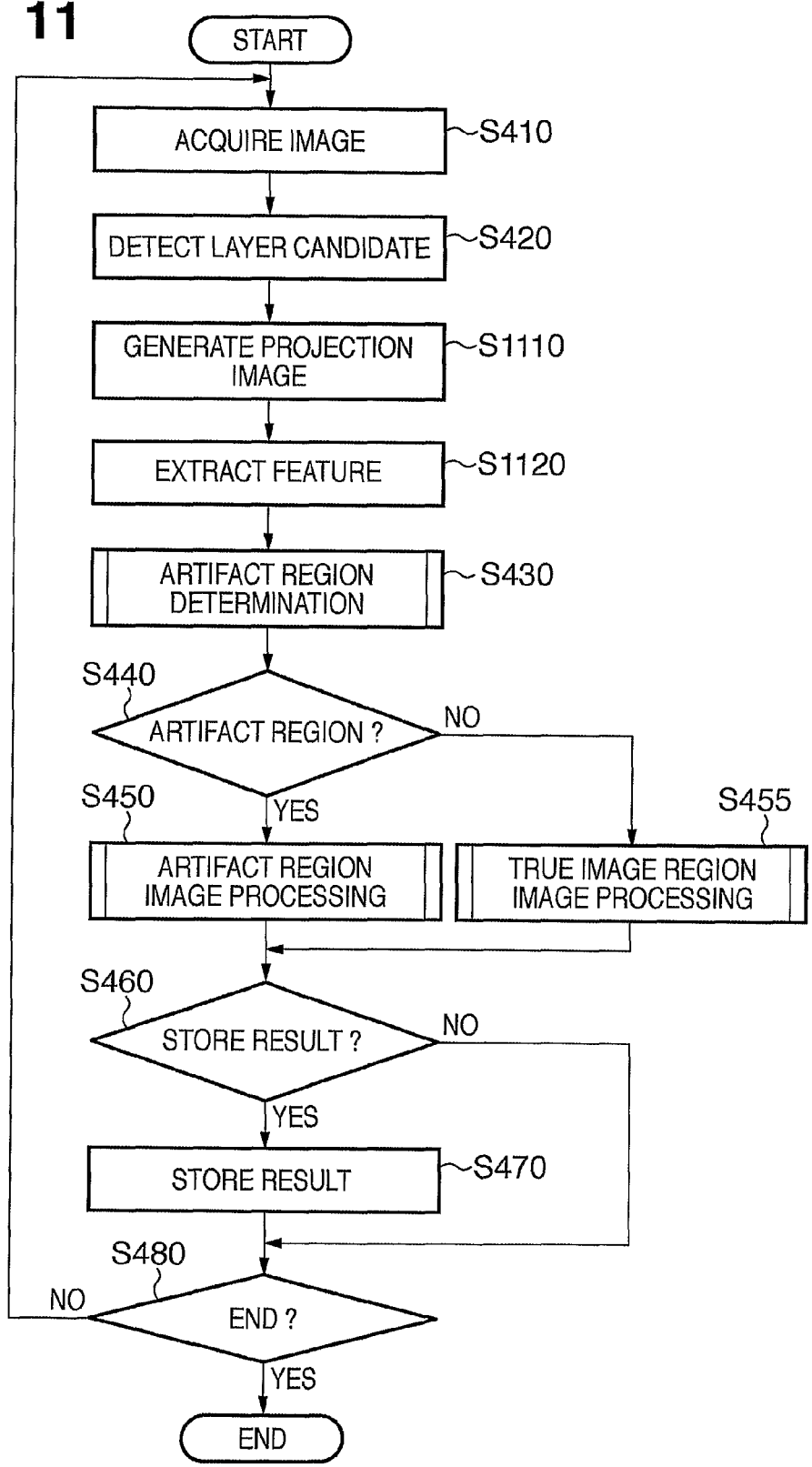
FIG. 11 is a flowchart showing the processing sequence of the image processing apparatus 10 according to the third embodiment.

The contents of image processing according to this embodiment will be described below with reference to the flowchart shown in FIG. 11. Note that most of steps of this flowchart are common to those in the flowchart of FIG. 4, and the same step numbers denote the common processes. A description of the common processes will not be repeated. In this embodiment, projection image generation process S1110 and feature extraction processing S1120 are executed between layer candidate detection processing in step S420 and artifact region determination processing in step S430 unlike in the first embodiment.

In step S1110, the projection image generation unit 335 generates an image by projecting a tomogram. More specifically, a projection image is defined by pixel values as values obtained by simply adding intensities of pixels on the tomogram in a positive direction of a z-axis. However, each pixel value of the projection image is not limited to such value, and the sum of intensities may be divided by the number of added pixels. Alternatively, a maximum value or minimum value of intensities at each depth position may be used as each pixel value of the projection image. Also, intensities of all pixels in the z-axis direction need not be added, and those only in an arbitrary range or between specific layers may be added.

In step S1120, a feature region where biological tissue such as a retina blood vessel in an eye to be examined or a morbid portion exists is extracted from the projection image generated by the projection image generation unit 335. Since the retina blood vessel has a thin linear structure, it is extracted using a filter that emphasizes the linear structure. In this case, a line segment emphasizing filter based on a contrast, for example, a filter which calculates a difference between an average value of image density values in a line segment defined as a structural element, and an average value in a local region that surrounds the structural element, is used. Note that a multi-valued region obtained as the processing result of the filter may be used as a blood vessel extraction result, or a region binarized using a certain threshold may be used as the extraction result.

However, the method of emphasizing the linear structure is not limited to this. For example, a differential filter such as a Sobel filter or Laplacian filter may be used. Eigenvalues of a Hessian matrix may be calculated for respective pixels of a density value image, and a linear region may be extracted from combinations of two eigenvalues obtained as results. Furthermore, an arbitrary known blood vessel extraction method such as tophat operations simply using a line segment as a structural element may be used.

Figure 12:
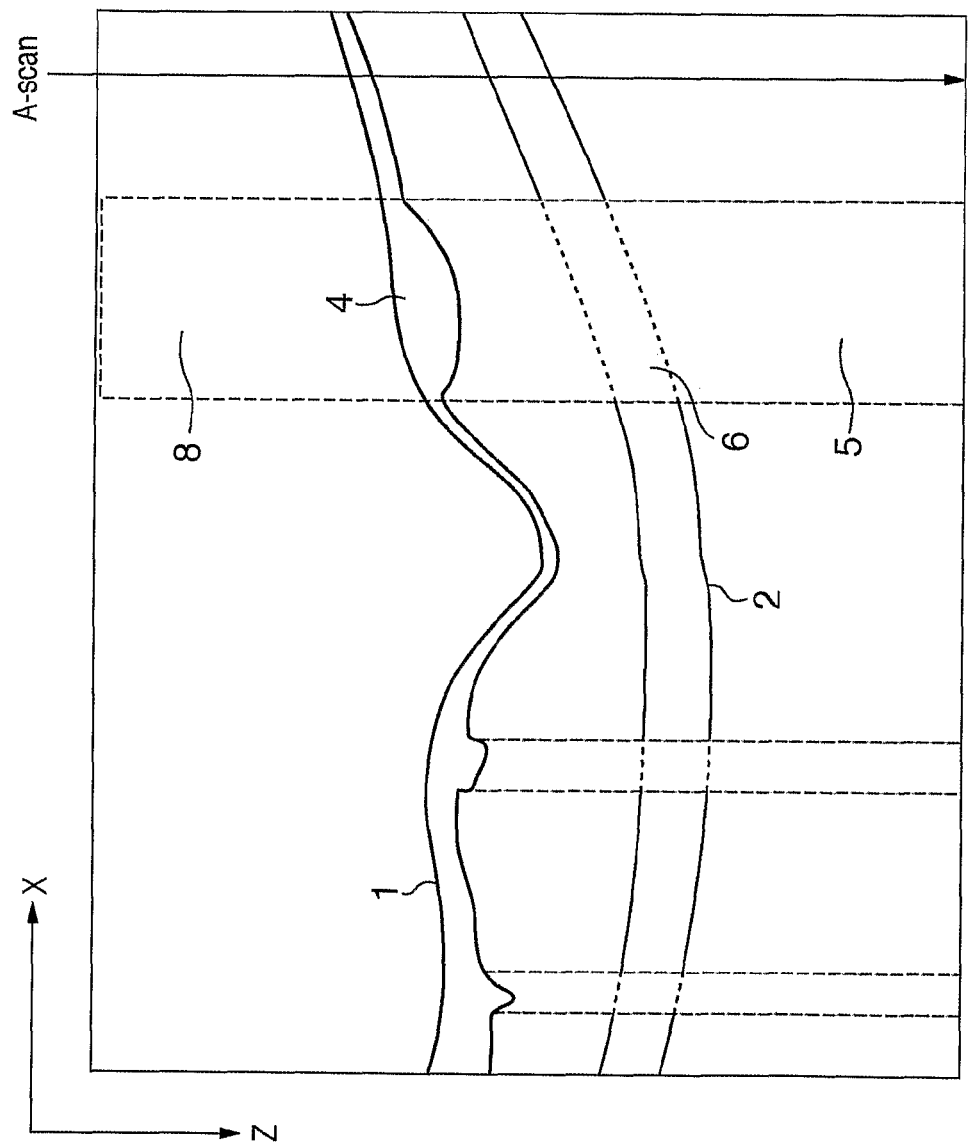
FIG. 12 is a view for explaining a determination method of an artifact region according to the third embodiment.

When a feature region (x, y) on the projection image calculated in step S1120 in this way is back-projected onto the tomogram, a back-projection region is obtained, as indicated by a dotted region 8 in FIG. 12. In general, intensity attenuation readily occurs on the positive direction side of the z-axis of the retina blood vessel. Therefore, when the position (in x-y directions) of the extracted feature is back-projected onto the tomogram, the back-projected dotted region 8 is more likely to include an artifact region 5. However, when an erroneously extracted region is back-projected, no intensity attenuation occurs in the back-projection region. Even when a correctly extracted retina blood vessel region is back-projected, intensity attenuation below the back-projection region is slight and has nearly no influence on layer extraction in some cases.

Hence, whether or not an artifact is generated in the back-projection region and near the boundary of that region is determined. If an artifact region is generated, a statistical amount associated with intensities in that region is calculated. Hence, the artifact region determination method in step S430 is basically the same as that in steps S610 to S640 of the first embodiment, except for a range of layer candidate points as calculation targets of a continuity. More specifically, the continuity calculation processing is executed not for all layer candidate points, but for the interior of the back-projection region and in the vicinity of the region in x-y directions.

According to the aforementioned arrangement, the image processing apparatus 10 of this embodiment specifies an artifact region from a tomogram and projection image, and executes image correction based on, for example, a intensity statistical amount in that region, thus obtaining an image from which a layer region included in the artifact region can be detected more easily.

Fourth Embodiment

Unlike in the third embodiment, this embodiment not only executes image correction in an artifact region after the artifact region is determined, but also detects a predetermined layer from the corrected image. This embodiment copes with the following points.

(i) When an artifact is generated due to a blood vessel (or bleeding), position information of a blood vessel (bleeding) region calculated from a projection image is mapped onto a tomogram, and an edge portion of an artifact region is searched for and specified from a surrounding region of the mapped region, thus allowing to calculate a range of the artifact region with higher precision.

(ii) Even in a region where an artifact is generated and intensities are attenuated, that region undergoes image correction to allow to easy detection of remaining edge information, and the edge information is detected from the corrected region, thus allowing to calculate a more precise layer position.

Figure 13:
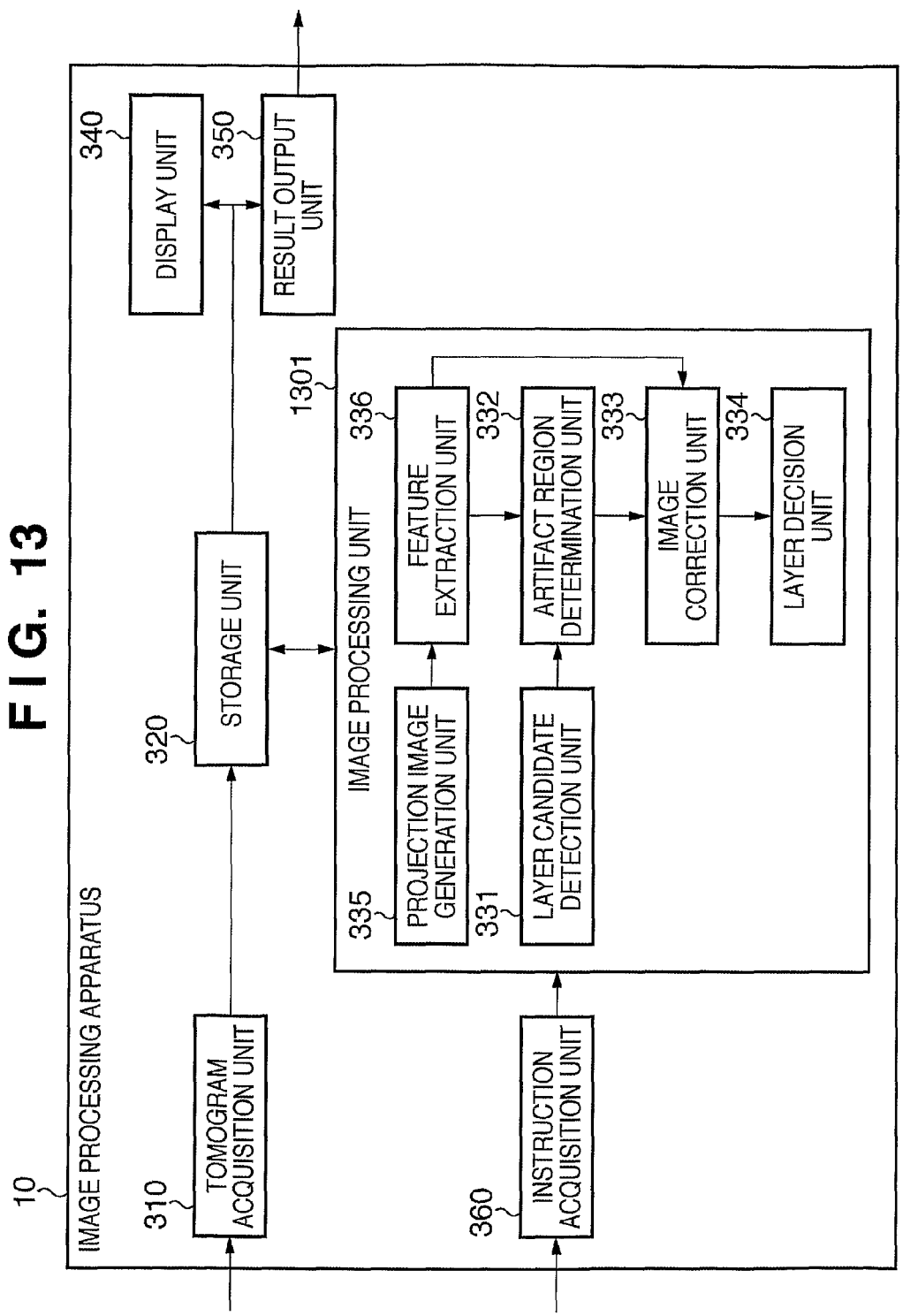
FIG. 13 is a block diagram showing the functional arrangement of an image processing apparatus 10 according to the fourth embodiment.

Since the arrangement of apparatus connected to an image processing apparatus 10 according to this embodiment is the same as that in the third embodiment, a description thereof will not be repeated. FIG. 13 is a functional block diagram of the image processing apparatus 10 according to this embodiment. An image processing unit 1301 of this embodiment includes a layer decision unit 334 unlike in the image processing unit 1001 of the third embodiment. The contents of image processing of this embodiment are the same as those in FIG. 13, except for processes in steps S450 and S455. Hence, only the processes in step S450 and S455 of this embodiment will be explained, and a description of other steps will not be given.

In step S450, as image processing in an artifact region, image correction, layer decision, layer geometry measurement, and result display processes are executed. The processing of this step is the same as that in steps S1010 to S1040 in the second embodiment, and a detailed description thereof will not be repeated. In step S455, as processing executed when no artifact is generated, a layer geometry is measured from a layer position acquired in step S420, and the layer position and layer geometry measurement result are superimposed on a tomogram. Details of the superimposing method are the same as those in steps S1110 to S1120 in the second embodiment, and a detailed description thereof will not be repeated.

According to the aforementioned arrangement, the image processing apparatus 10 of this embodiment specifies an artifact region from a tomogram and projection image, and executes image correction in that region. Since the apparatus detects image features of a layer from the correction result, the layer position in that region can be calculated more precisely.

Fifth Embodiment

In this embodiment, position information of tissue or a morbid portion extracted from at least one of a surface image of an eye to be examined and a projection image is back-projected onto a tomogram to narrow down artifact candidate regions in advance, in addition to the third embodiment. This is because when a morbid portion such as an exudate, which is especially easily extracted from a surface image, is generated, an exudate region is calculated using a surface image, and an edge portion of an artifact region is searched for and specified from a surrounding region of the extracted morbid portion, thus allowing to calculate a range of an artifact region with higher precision.

Figure 14:
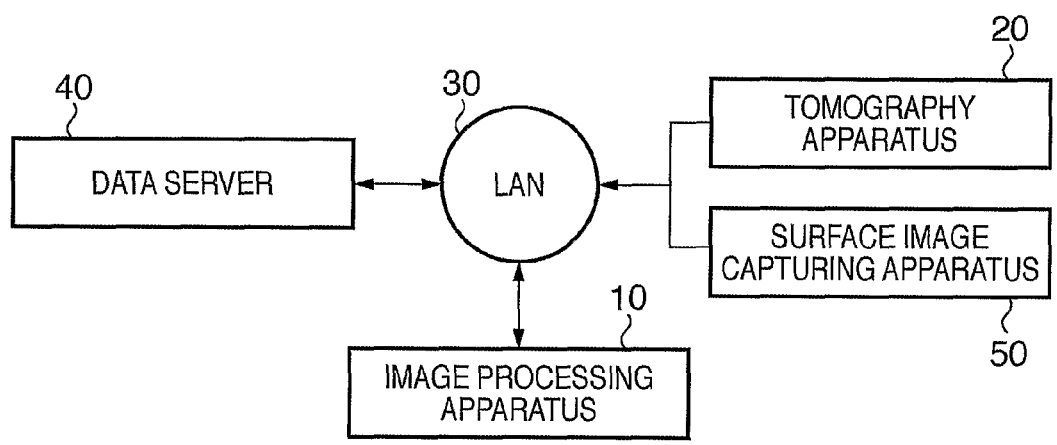
FIG. 14 is a block diagram showing the arrangement of apparatus connected to an image processing apparatus 10 according to the fifth embodiment.
Figure 15:
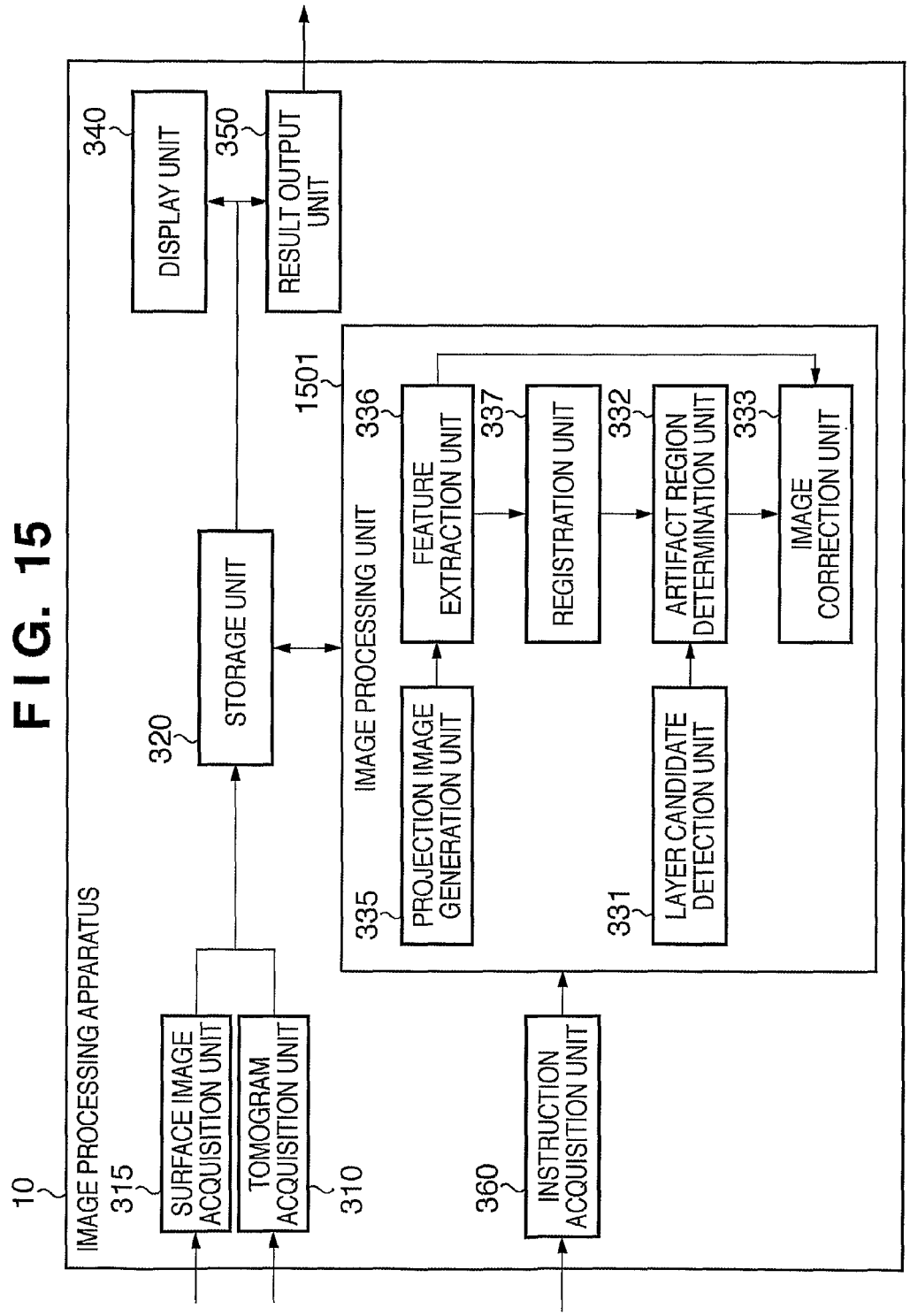
FIG. 15 is a block diagram showing the functional arrangement of the image processing apparatus 10 according to the fifth embodiment.

FIG. 14 shows the arrangement of apparatus connected to an image processing apparatus 10 according to this embodiment. In this embodiment, the arrangement includes a surface image capturing apparatus 50 in addition to a tomography apparatus 20 unlike in the third embodiment. The surface image capturing apparatus 50 captures a surface image of an eye portion, and includes, for example, a fundus camera or SLO (Scanning Laser Ophthalmoscope). FIG. 15 is a functional block diagram of the image processing apparatus 10 of this embodiment. The image processing apparatus 10 of this embodiment includes a surface image acquisition unit 315, and an image processing unit 1501 includes a registration unit 337 unlike in the arrangement of the image processing apparatus 10 of the third embodiment.

Figure 16:
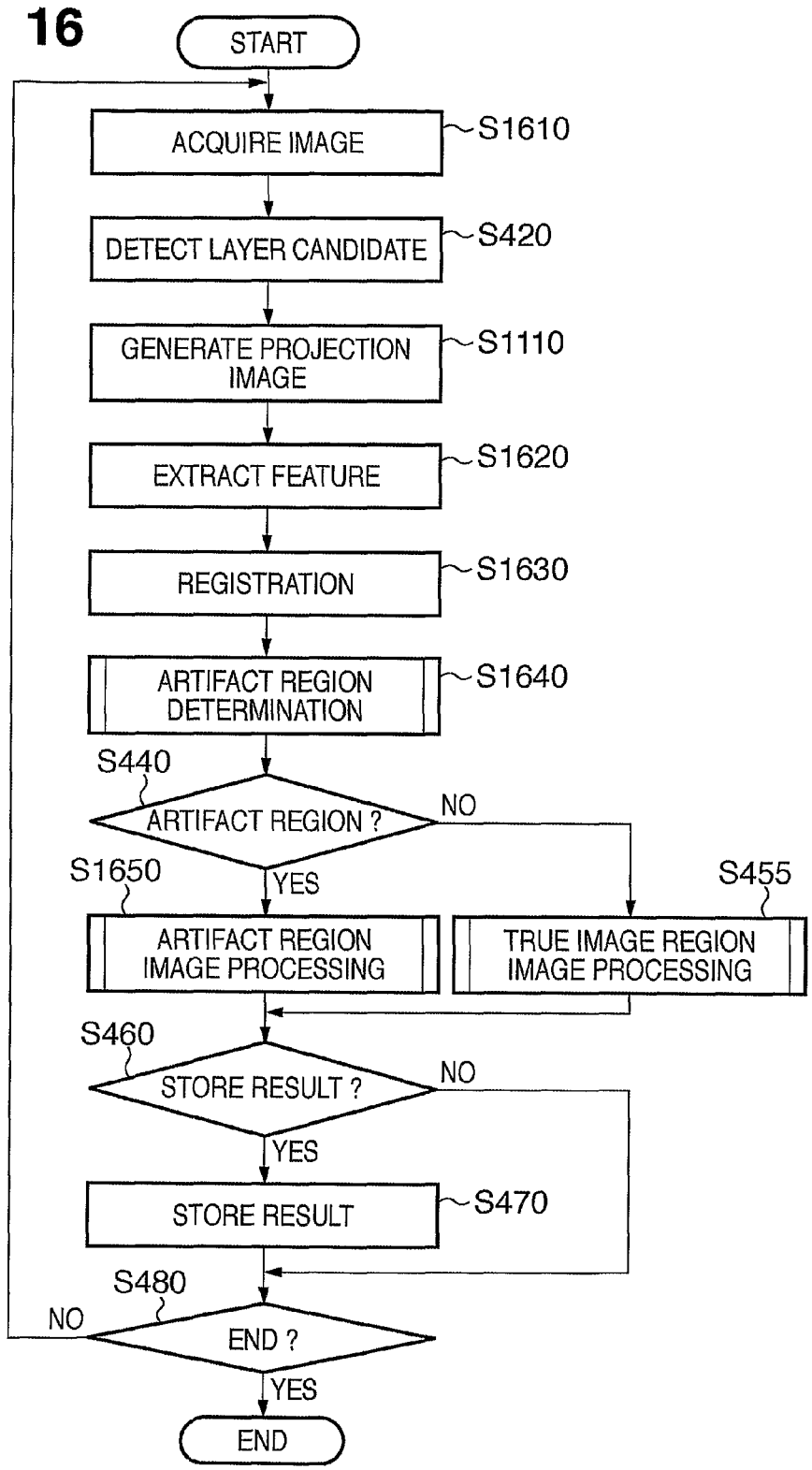
FIG. 16 is a flowchart showing the processing sequence of the image processing apparatus 10 according to the fifth embodiment.

Image processing in the image processing unit 1501 of this embodiment will be described below with reference to the flowchart shown in FIG. 16. The image processing sequence of this embodiment is nearly the same as that shown in FIG. 11, except for processes in steps S1610 to S1650. Hence, the processes in these steps will be described below.

In step S1610, in addition to acquisition of a tomogram by a tomogram acquisition unit 310, the surface image acquisition unit 315 requests the surface image capturing apparatus 50 to transmit a surface image, and acquires a surface image transmitted from the surface image capturing apparatus 50. Assume that a fundus camera image is input as the surface image. The unit 315 transmits the acquired information to a storage unit 320.

In step S1620 that follows projection image generation processing in step S1110, the feature extraction unit 336 extracts tissue such as a blood vessel or a morbid region such as an exudate from the surface image acquired by the surface image acquisition unit 315. Since a retina blood vessel has a linear structure, it is extracted using a filter that emphasizes the linear structure. Since the linear structure extraction method is the same as that in step S1120, a description thereof will not be given. Since an exudate exists as a granular high-intensity region, it is calculated by morphology operations such as tophat transformation. In this case, an exudate region is obtained as a high-intensity multi-valued region by the morphology operations, and the multi-valued region itself may be used as an extraction result or a region binarized using a certain threshold may be used as the extraction result. However, the exudate extraction method is not limited to this, and an exudate may be identified by an identifier such as a Support Vector Machine or an identifier ensemble such as Ada Boost using intensities of the surface image and an output result of a known filter which emphasizes a contrast as feature amounts.

In step S1630, the registration unit 337 performs registration between the projection image and surface image so as to associate the coordinates of the projection image with those of the surface image. At the time of registration, an evaluation function, which represents a similarity between two images, is defined in advance, and images are deformed to obtain the best evaluation value. As the similarity evaluation method, a method of evaluating a similarity based on pixel values using a mutual information content is used. However, the present invention is not limited to such specific method, and a mean square error, correlation coefficients, or an overlapping area of blood vessel regions, distances between branch portions of blood vessels, or the like, which are extracted from the surface image and projection image by the feature extraction unit 336, may be used. Image deformation is implemented by translating or rotating images or changing an enlargement factor under the assumption of affine transformation.

Figure 17A:
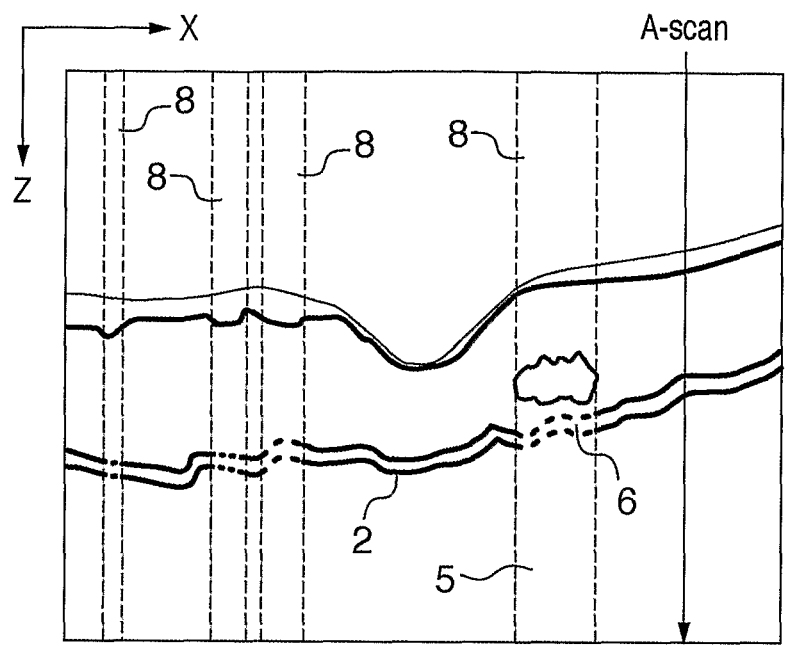
FIGS. 17A and 17B are views for explaining a determination method of an artifact region according to the fifth embodiment.
Figure 17B:
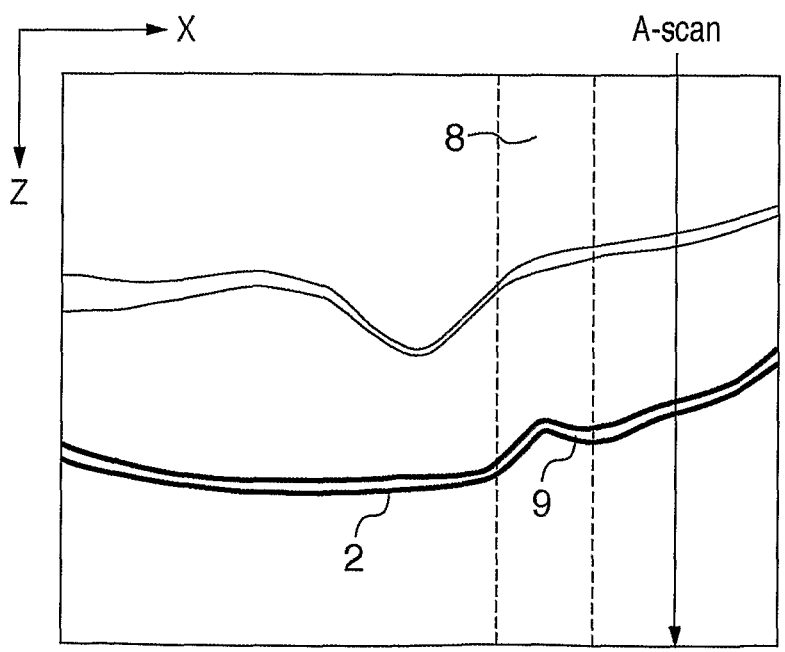

In step S1640, the blood vessel or exudate extraction result from the surface image calculated in step S1620 is back-projected onto a tomogram using registration parameters calculated in step S1630. As a back-projection region, regions indicated by dotted regions 8 in FIG. 17A are obtained. In general, since intensity attenuation often occurs on the positive direction side of the z-axis of a retina blood vessel, when coordinates (in x-y directions) and intensities of each feature-extracted region are back-projected onto a tomogram, each back-projected dotted region 8 is more likely to include an artifact. However, when an exudate is extracted from the surface image like in this embodiment, a granular high-intensity region such as a druse is likely to be erroneously extracted in exudate candidate regions. In this case, no intensity attenuation in a layer region occurs, as shown in FIG. 17B. Even when a correctly extracted retina blood vessel region is back-projected, intensity attenuation below the back-projection region is slight and has nearly no influence on layer extraction in some cases. Hence, whether or not an artifact is generated in the back-projection region and near the boundary of that region is determined. If an artifact is generated, a statistical amount of intensities in that region is calculated.

The artifact region determination method is basically the same as that in case of steps S610 to S640 of the first embodiment, but a range of layer candidate points as calculation targets of a continuity is different from the first embodiment. More specifically, the continuity calculation processing is executed not for all layer candidate points, but for the interior of the back-projection region and in the vicinity of the region in x-y directions. Note that the artifact region may be determined with reference to information obtained from the projection image and a fundus image in addition to that obtained from only the tomogram. For example, when a retina blood vessel region obtained from the projection image overlaps that obtained from the fundus image, it may be considered that the region is more likely to be a blood vessel, and an edge portion of that region may be determined to be discontinuous. Alternatively, a linear sum of a continuity value calculated from the tomogram and a value of a degree of overlapping of the blood vessel regions may be calculated, and may be binarized using a threshold, so as to determine a continuity.

Since artifact region image processing in step S1650 displays a correction result after image correction, that is, it adopts basically the same sequence as in the first embodiment, a detailed description thereof will not be given. However, in this embodiment, at the time of image correction of the artifact region, information obtained from the fundus image may also be referred to. For example, when intensities of an exudate are very high on the fundus image, since intensities are more likely to be attenuated on the positive direction side of the z-axis of layer candidate points even on the tomogram, intensities are amplified or emphasized in proportion to intensity signal values of an exudate region. In this case, as intensities of an exudate region, pixel values of that region on the fundus image are directly referred to. However, intensities of the exudate region are not limited to these values, and values (multi-valued data) of the processing result obtained by, for example, morphology operations or the like may be referred to.

According to the aforementioned arrangement, the image processing apparatus 10 of this embodiment executes image correction based on a statistical amount of intensities in an artifact region specified using a surface image and projection image, thereby obtaining an image from which a layer region that exists in the region can be detected more easily.

Sixth Embodiment

This embodiment not only executes image correction of an artifact region in the fifth embodiment, but also detects a predetermined layer from the corrected image. Especially when an artifact is generated due to an exudate, this embodiment uses the following points.

(i) Position information of an exudate region calculated from a surface image is mapped onto a tomogram, and an edge portion of an artifact region is searched for and specified from a surrounding region of that region, thereby calculating a range of the artifact region with higher precision.

(ii) Even in a region where an artifact is generated and intensities are attenuated, that region undergoes image correction to allow to easy detection of remaining edge information, and the edge information is detected from the corrected region, thus allowing to calculate a more precise layer position.

Figure 18:
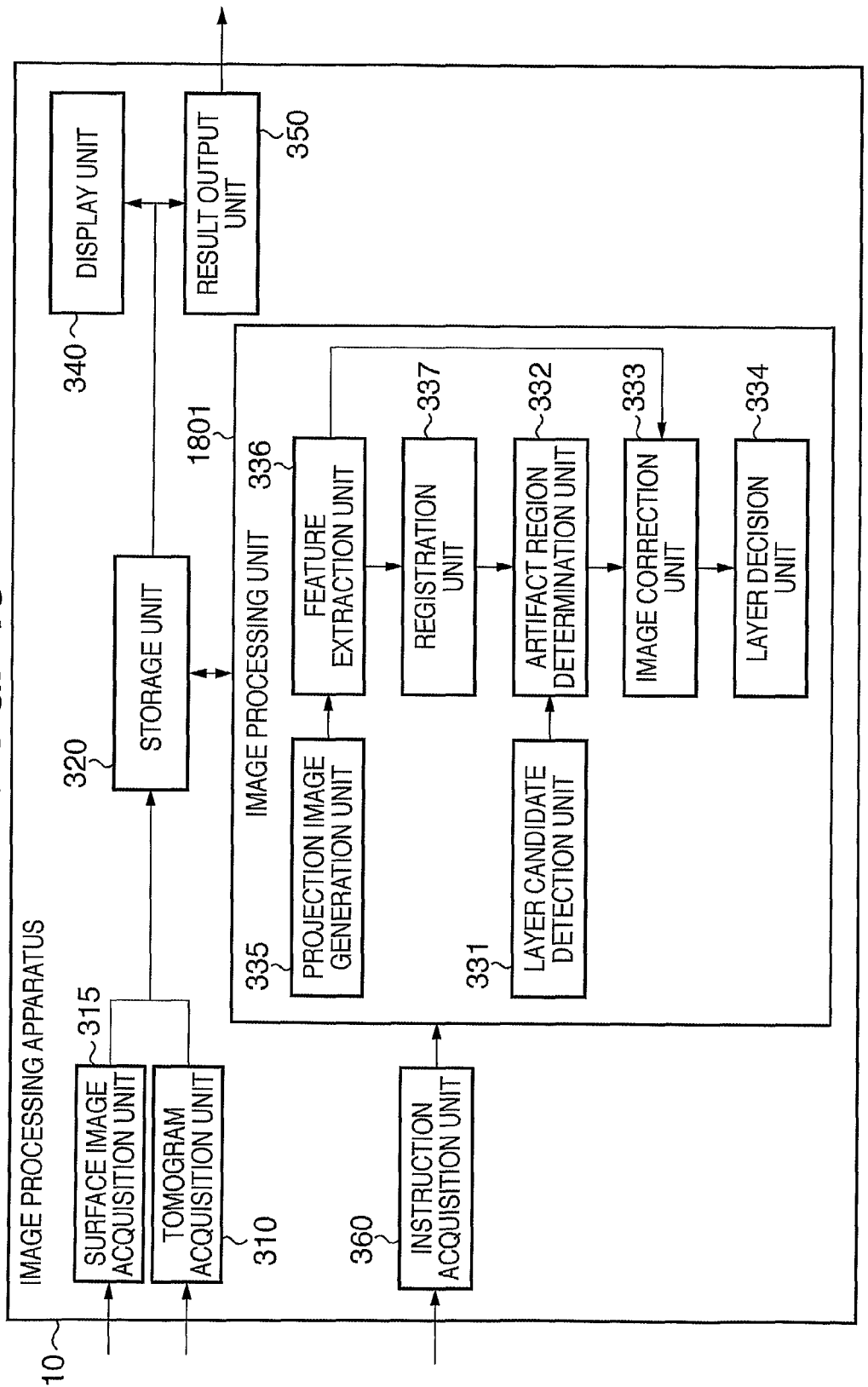
FIG. 18 is a block diagram showing the functional arrangement of an image processing apparatus 10 according to the sixth embodiment.

The arrangement of apparatus connected to an image processing apparatus 10 according to this embodiment is the same as that in the fifth embodiment. FIG. 18 is a functional block diagram of the image processing apparatus 10 according to this embodiment. An image processing unit 1801 of this embodiment includes a layer decision unit 334 unlike in the image processing unit 1501 of the fifth embodiment. The image processing sequence of this embodiment is the same as that shown in FIG. 16 except for processes in steps S1650 and S455. Hence, only the processes in steps S1650 and S455 will be explained, and a description of other steps will not be repeated.

In step S1650, as image processing in an artifact region, image correction, layer decision, layer geometry measurement, and result display processes are executed. The processing of this step is the same as that in steps S1010 to S1040 in the second embodiment, and a detailed description thereof will not be repeated. However, in this embodiment, image correction can be executed also using information obtained from a fundus image in step S1010. A practical sequence for referring to information obtained from a fundus image at the time of image correction is the same as that in case of step S1650 in the fifth embodiment, and a description thereof will not be repeated.

In step S455, as processing to be executed when no artifact is generated, a layer geometry is measured from a layer position acquired in step S420, and the layer position and the layer geometry measurement result are superimposed on the tomogram. The superimposing method in this case is the same as that in the second embodiment, and a detailed description thereof will not be repeated.

According to the aforementioned arrangement, the image processing apparatus 10 executes image correction in an artifact region specified from a surface image and projection image. By detecting image features of a layer from the correction result, the layer position in the region can be calculated more precisely.

Seventh Embodiment

In this embodiment, an artifact region is determined from a tomogram of an eye to be examined, and a layer position in the artifact region is calculated using both pieces of information in consideration of intensities in the artifact region and a layer geometry around the region.

Figure 19:
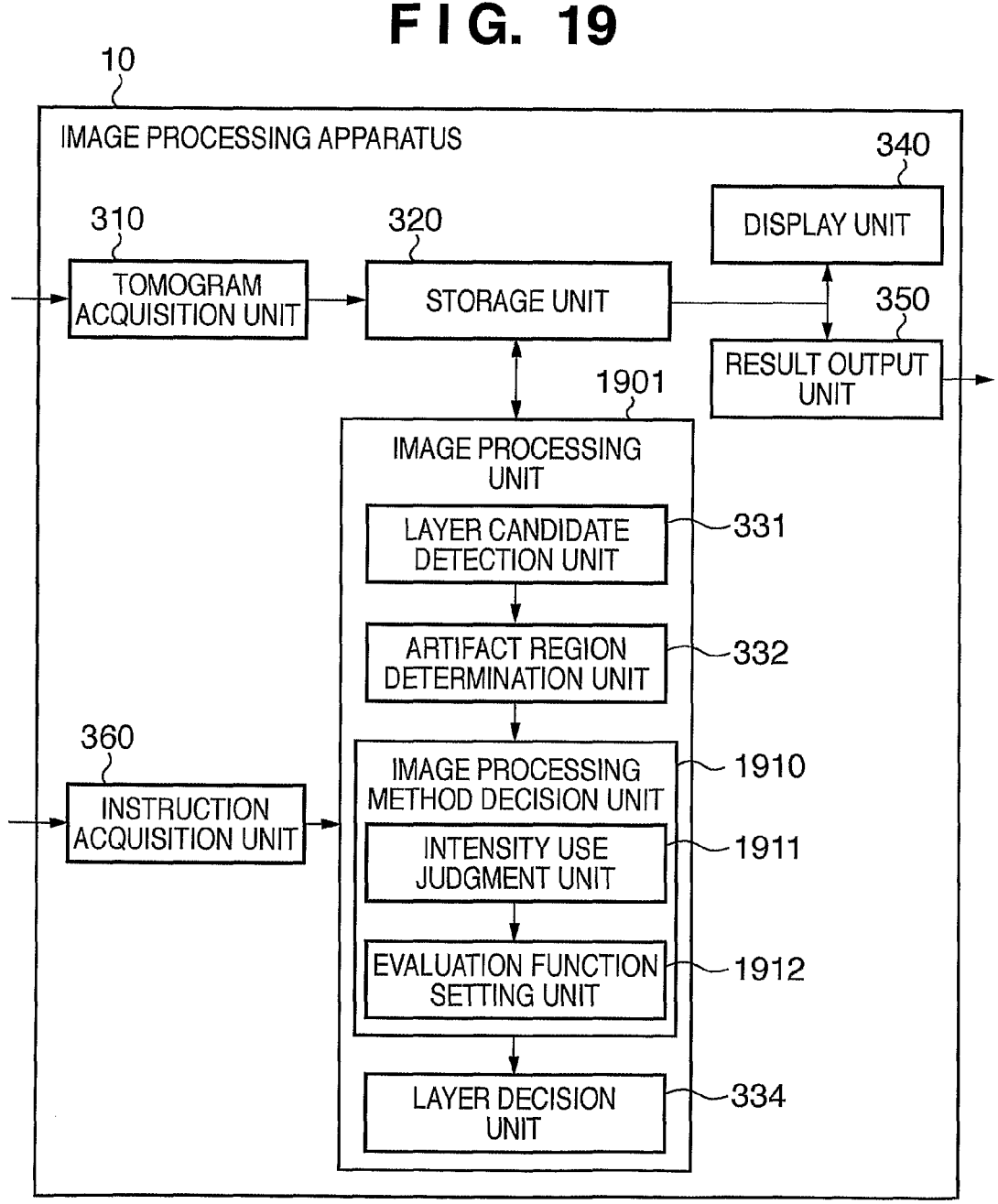
FIG. 19 is a block diagram showing the functional arrangement of an image processing apparatus 10 according to the seventh embodiment.

Since the arrangement of apparatus connected to an image processing apparatus 10 according to this embodiment is the same as that shown in FIG. 2 of the first embodiment, a description thereof will not be given. FIG. 19 is a functional block diagram of the image processing apparatus 10 according to this embodiment. Referring to FIG. 19, an image processing unit 1901 of this embodiment includes an image processing method decision unit 1910 in place of the image correction unit 333, and additionally includes a layer decision unit 334 unlike in the arrangement of the image processing unit 330 of the image processing apparatus 10 of the first embodiment. The image processing method decision unit 1910 includes a intensity use judgment unit 1911 and evaluation function setting unit 1912. The functions of respective blocks, which configure the image processing apparatus 10, will be described below with reference to the flowchart shown in FIG. 20 in association with the practical processing sequence to be executed by the image processing apparatus 10 of this embodiment.

The image processing sequence of this embodiment will be described below. Note that the processing sequence of this embodiment is the same as that in the flowchart shown in FIG. 4 except for processes in steps S2010 to S2030. Hence, only steps S2010 to S2030 will be explained below, and a description of other steps will not be repeated.

In step S2010, an artifact region determination unit 332 branches processes according to a determination result obtained in step S430. That is, for a layer candidate point for which it is determined that an artifact is generated, the unit 332 transmits a signal to instruct the image processing method decision unit 1910 to execute predetermined processing. On the other hand, if the unit 332 determines a true image region where no artifact is generated, it transmits a signal to instruct a display unit 340 to execute predetermined processing.

In step S2020, the image processing unit 1901 executes analysis processing when an artifact is generated near candidate points of a predetermined layer. The processing of this step will be described in detail later using the flowchart shown in FIG. 21. In step S2030, the display unit 340 superimposes a layer determination result on a tomogram. When boundaries of a layer are indicated by lines, lines of a predetermined color may be used for the respective boundaries, or a region of a layer may be presented with a translucent color without explicitly indicating boundaries. Note that upon making such display, an arrangement that allows to select a section of interest using, for example, a GUI is desirably adopted. Also, these results may be three-dimensionally displayed using a known volume rendering technique.

Furthermore, a retina layer thickness can be measured by calculating distances for respective coordinates (x, y) between a calculated layer candidate point sequence corresponding to a retinal pigment epithelium, and an inner limiting membrane 1 calculated in step S420. In this case, the display unit 340 presents information associated with the measured layer geometry as a distribution map of layer thicknesses with respect to an entire 3D tomogram (x-y plane). However, the present invention is not limited to such specific display method. For example, the display unit 340 may display areas of respective layers in a section of interest in synchronism with the display process of the detection result. Alternatively, the display unit 340 may display an entire volume or may calculate and display a volume in a region which is designated by an operator on the x-y plane.

The artifact region image processing in step S2020 of this embodiment will be described below. In this embodiment, a Deformable Model is applied to a layer position so that the layer position can be calculated even in a tomogram including noise. An example using Snakes as a Deformable Model will be described below. In this case, the layer position is decided by minimizing a linear sum of evaluation function values associated with a model geometry and those associated with intensities near control points which configure the model.

As evaluation functions associated with a geometry, linear sums of differences and secondary differential values of control point positions which configure a model are used. The model geometry becomes smoother with decreasing linear sums. As evaluation functions associated with intensity, values obtained by assigning the negative sign to intensity gradients near control points that configure a model are used. This is to reduce evaluation function values with decreasing distance to an edge. Weights of evaluation functions used to deform a Deformable Model are normally set to be fixed values irrespective of whether or not control points that configure the model are included in an artifact region. In this case, since intensities in the artifact region are attenuated, and a change in intensity is small in that region, a layer position is practically decided based on the magnitudes of the evaluation function values associated with the model geometry. When information of, for example, an edge remains in the artifact region, the layer position is to be decided while placing importance on information associated with intensity (in preference to a case in which the layer position is calculated based on a smoothness of the model geometry), thereby detecting the layer geometry more precisely. For this reason, weights of the evaluation functions associated with intensity are set to be larger than those for a true image region according to the degree of attenuation of intensities at control points in the artifact region.

However, when intensities in the artifact region are low, and nearly no information of, for example, an edge remains, intensity information of, for example, an edge cannot be used at the time of decision of the layer position. Hence, the weights of the evaluation functions associated with intensity are not increased, and the layer position is to be decided based on the magnitudes of the function evaluation values associated with the model geometry.

Figure 21:
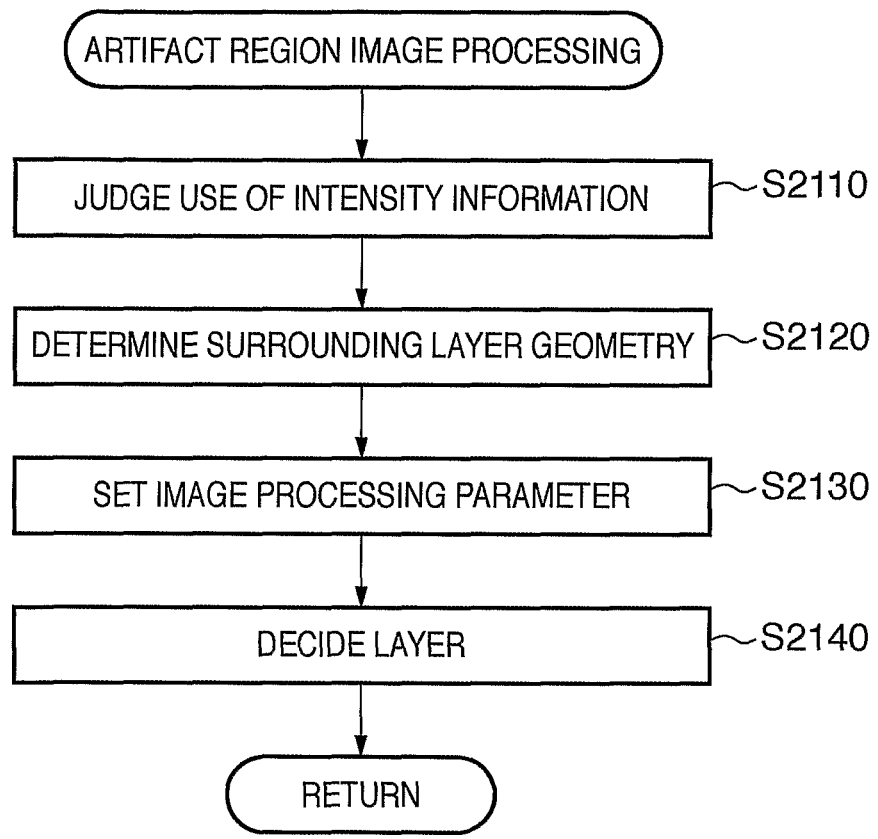
FIG. 21 is a flowchart showing the image processing sequence for a region determined as an artifact region according to the seventh embodiment.

A method of practically setting weights of respective evaluation functions of the Deformable Model will be described below with reference to the flowchart shown in FIG. 21.

Figure 6:
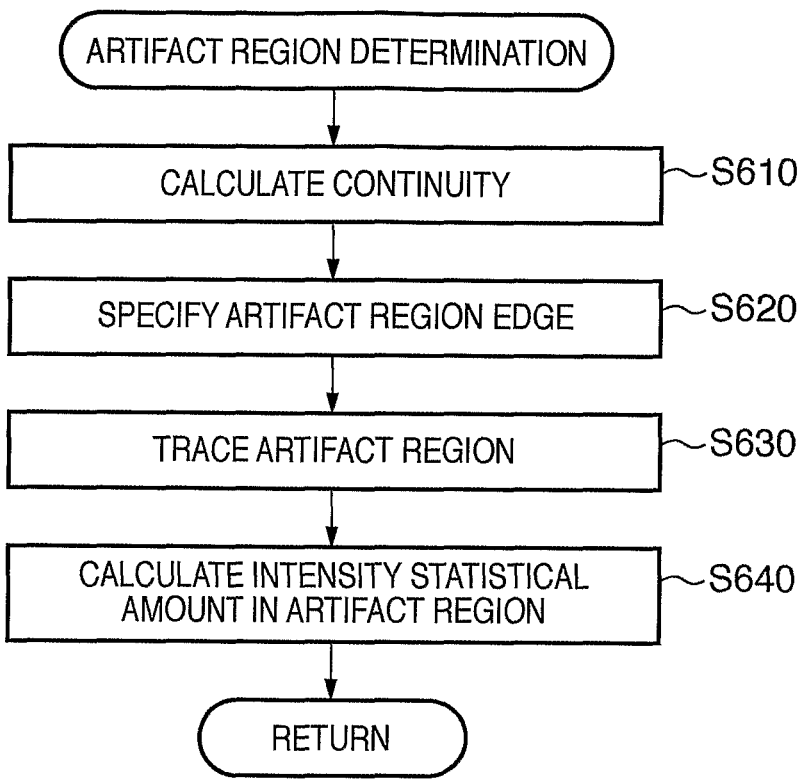
FIG. 6 is a flowchart showing the image processing sequence required to determine an artifact region according to the first embodiment.

In step S2110, the image processing method decision unit 1910 reads out, from a storage unit 320, a statistical amount associated with intensities in an artifact region, which is calculated in step S640 of the flowchart of FIG. 6, that shows details of the artifact region determination processing in step S430. The unit 1910 judges based on the statistical amount whether intensity information is used at the time of layer detection since an (attenuated) edge remains in that region or intensity information of, for example, an edge is not used since intensity is deficient.

More specifically, an index E(i) is calculated, and if E(i)=1, it is judged that intensity information is used at the time of decision of the layer position; if E(i)=0, it is judged that intensity information is not used. The index E(i) is given by:

$$E(i) = \begin{cases} 1 & \left(\frac{F_i}{B} > T_s\right) \\ 0 & \left(\frac{F_i}{B} \leq T_s\right) \end{cases} \quad (8)$$

where i is a control point number of the Deformable Model, B is a statistical amount associated with intensities in a background region (for example, a region on the negative direction side of a z-axis of the inner limiting membrane 1), and Fi is a statistical amount associated with intensities in an artifact region to which a control point i belongs. As for the statistical amount associated with intensities, a maximum value is used. Also, $T_s$ is a threshold.

Note that the statistical amount associated with intensities is not limited to this. For example, an average value, variance, or standard deviation may be used. Also, the artifact region may be divided into arbitrary local regions, and statistical amounts of intensities in local regions to which respective control points belong may be used as Fi.

In step S2120, the image processing method decision unit 1910 acquires information associated with an unevenness of a layer candidate point sequence around the artifact region.

This is because if a layer geometry around the artifact region has an unevenness, an unevenness is likely to be also generated in the region, and the layer position has to be calculated by lowering weights associated with evaluation of smoothness of the geometry. As a method of calculating a practical unevenness of the layer geometry, a statistical amount associated with angles between layer candidate points around the artifact region is calculated. In this case, a maximum value is used as the statistical amount.

Figure 22:
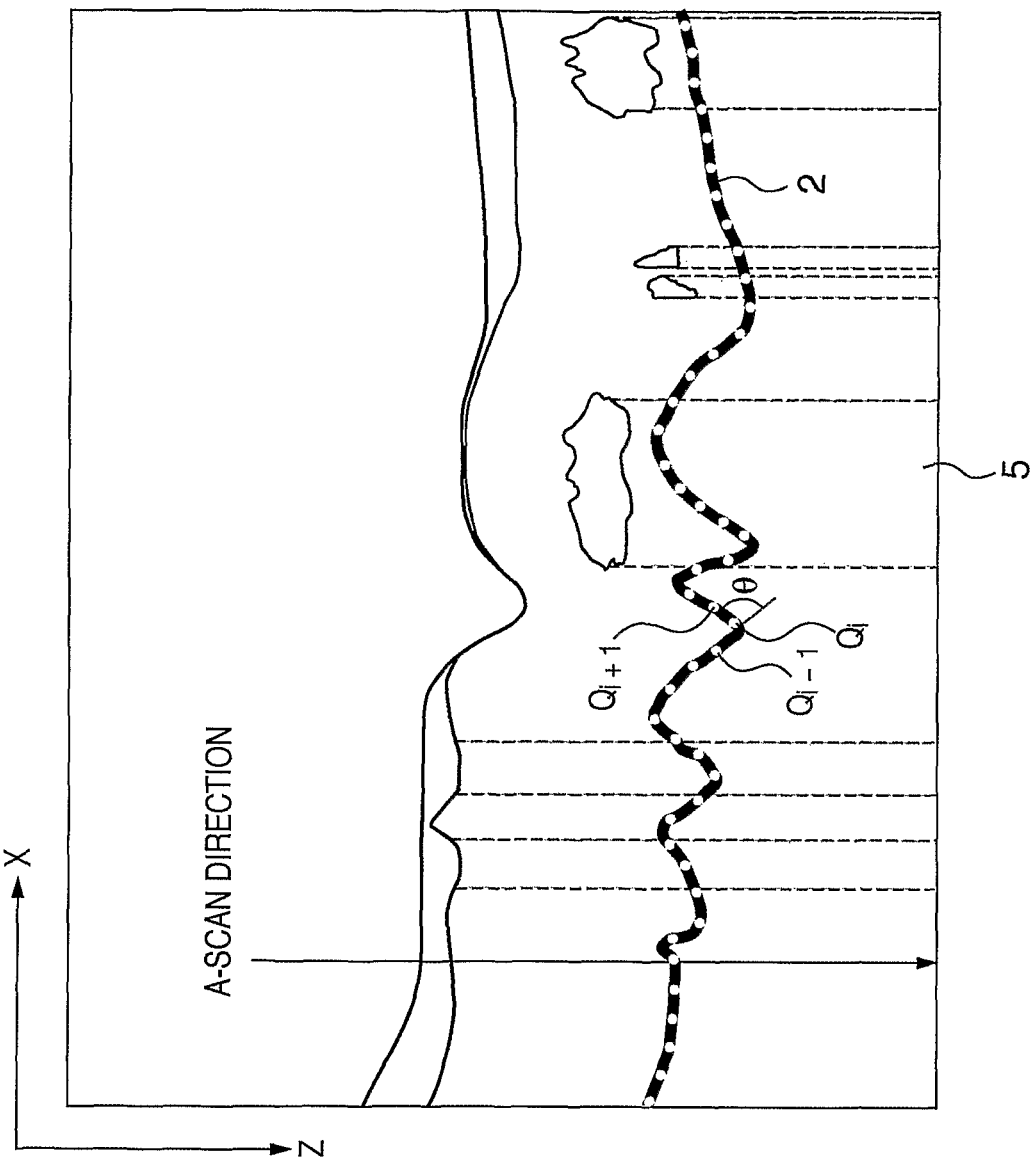
FIG. 22 is a view for explaining a method of measuring an uneven geometry of a layer according to the seventh embodiment.

An angle between layer candidate points at a layer candidate point i is calculated as an angle $\theta_i$ between a line segment obtained by extending a line segment to the $Q_{i-1}$–$Q_i$ side, and a line segment $Q_i$–$Q_{i+1}$, as shown in FIG. 22. The unevenness is larger with increasing $\theta_i$. Such angle calculation is executed for respective layer candidate points around the artifact region, and a maximum value of the calculated angles is used as an index which represents a degree of unevenness of the layer candidate point sequence. Note that the index associated with the degree of unevenness is not limited to the angle between layer candidate points, and a statistical amount (an average, variance, maximum value, etc.) of secondary differential values ($Q_{i-1}$–$2Q_i$+$Q_{i+1}$) at the layer candidate point positions may be calculated. Alternatively, an extremum or the number of inflection points when the layer candidate around the artifact region is regarded as a curve may be calculated. The statistical amount associated with the degree of unevenness of the layer candidate points is not limited to the maximum value. For example, an average value, variance, or standard deviation may be used.

In step S2130, the image processing method decision unit 1910 sets weights of the evaluation functions of the Deformable Model using the judgment result in step S2110 and the index associated with the degree of unevenness of the layer geometry calculated in step S2120. As the weights of the evaluation functions associated with the geometry, values, which are inversely proportional to the index representing the degree of unevenness of a layer geometric model calculated in step S2120, are set. The weights of the evaluation functions associated with intensities are set as follows according to the judgment result associated with use of intensity information in the artifact region calculated in step S2110.

(i) When intensity information in artifact region is used upon deciding layer position The weights of the evaluation functions associated with intensity are increased in accordance with degrees of attenuation of intensities in the artifact region. Then, values proportional to a ratio $T_s/F_s$ between a intensity statistical amount $F_s$ in the region calculated in step S640 and a intensity statistical amount $T_s$ in a true image region are set as the weights of the evaluation functions associated with intensity. However, the setting method of the weights of the evaluation functions associated with intensity is not limited to this. For example, an arbitrary weight function may be set as long as a relationship of a decreasing function is established between $F_s$ and the weights of the evaluation functions associated with intensity.

(ii) When intensity information in artifact region is not used upon deciding layer position In the artifact region, the weights of the evaluation functions associated with intensities of a geometric model are set to be the same values as those of a true image region. Note that the setting method of the weights of the evaluation functions associated with intensities in (ii) is not limited to this. For example, the weights of the evaluation functions associated with intensities may be reduced or may be set to zero.

In step S2140, the layer decision unit 334 calculates evaluation values according to the weights of the evaluation functions set in step S2130, and makes iterative calculations using an optimization method such as a Greedy Algorithm, thus minimizing the evaluation function values. When a change amount of the evaluation values is less than a predetermined value or when the iterative calculation count exceeds a predetermined count, the unit 334 ends deformation of the layer geometric model, and decides the position of the layer geometric model at the end timing as a layer position.

Note that these geometric models may be calculated as either 2D or 3D curve models. This embodiment has explained the example using Snakes as a Deformable Model, but Level Set may be used. Furthermore, arbitrary methods may be used as long as they set the weights of evaluation functions associated with intensities in a model-based segmentation method which refers to intensities upon deformation of a model.

According to the aforementioned arrangement, the image processing apparatus 10 specifies an artifact region, and executes image processing in consideration of an unevenness of a layer geometry around the region and edge information in the region, thus calculating a layer position with higher precision than the conventional method.

Eighth Embodiment

In this embodiment, upon calculating a layer position in an artifact region, whether or not to use intensity information of, for example, an edge in the region is judged. When intensity information is used, intensities in the region are corrected, and the layer position is then calculated. When intensity information is not used, the layer position is calculated by interpolation. This embodiment covers the following points.

(i) In a blood vessel or small exudate region where intensities are attenuated but are not deficient, intensities are converted to facilitate use of information of, for example, a remaining edge, and a layer position is then detected, thus calculating a more precise layer position.

(ii) In a large exudate or heavy bleeding region where intensities are deficient and edge information cannot be used, surrounding layer positions are interpolated in consideration of the generation position of an artifact region and surrounding layer geometries, thus calculating a more precise layer position.

Figure 23:
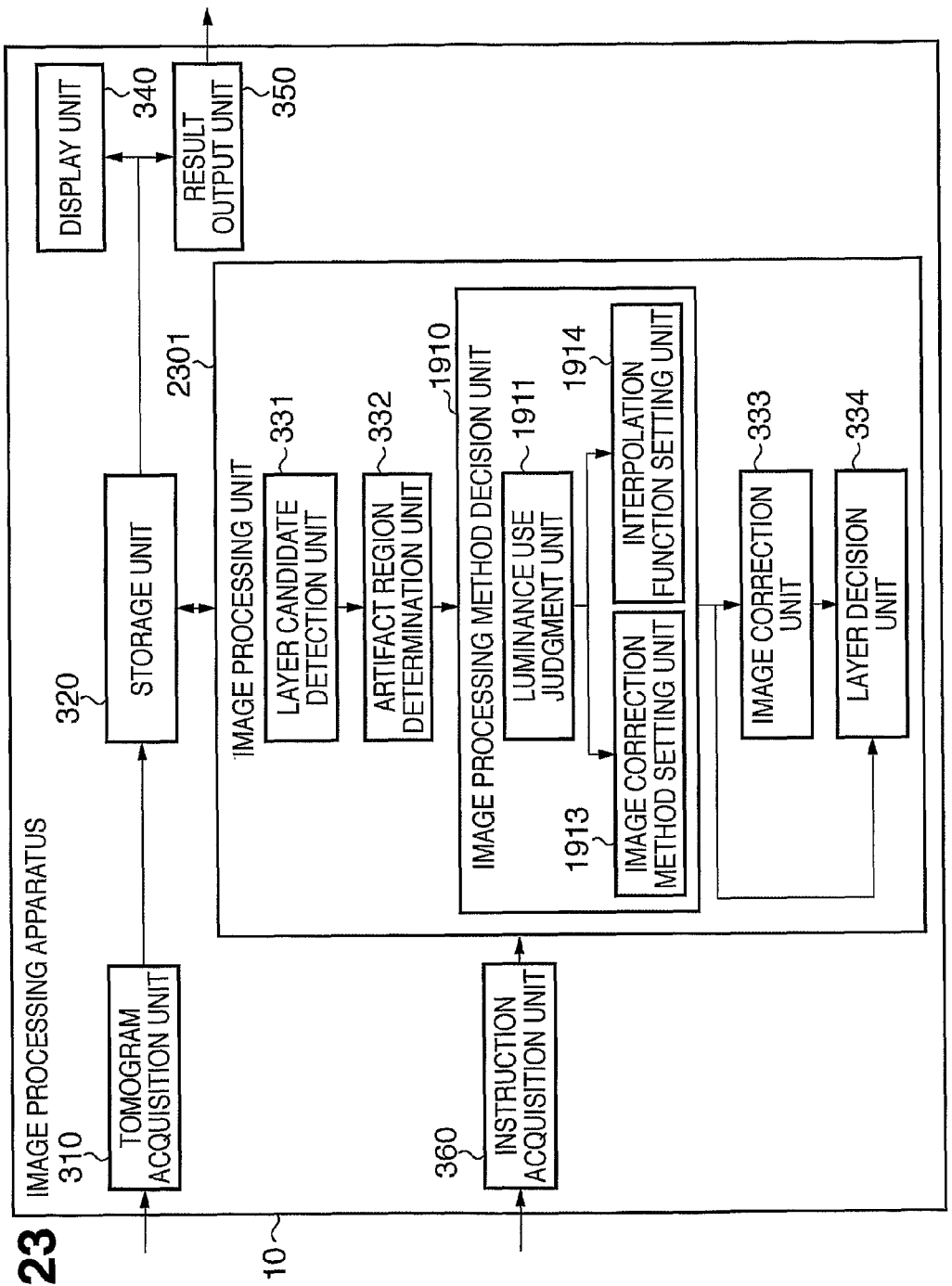
FIG. 23 is a block diagram showing the functional arrangement of an image processing apparatus 10 according to the eighth embodiment.

Since the arrangement of apparatus connected to an image processing apparatus 10 according to this embodiment is the same as that in the seventh embodiment, a description thereof will not be repeated. FIG. 23 is a functional block diagram of the image processing apparatus 10 according to this embodiment. In this embodiment, an image processing unit 2301 includes an image correction unit 333, and an image processing method decision unit 1910 includes an image correction method setting unit 1913 and interpolation function setting unit 1914 unlike in the seventh embodiment.

Figure 20:
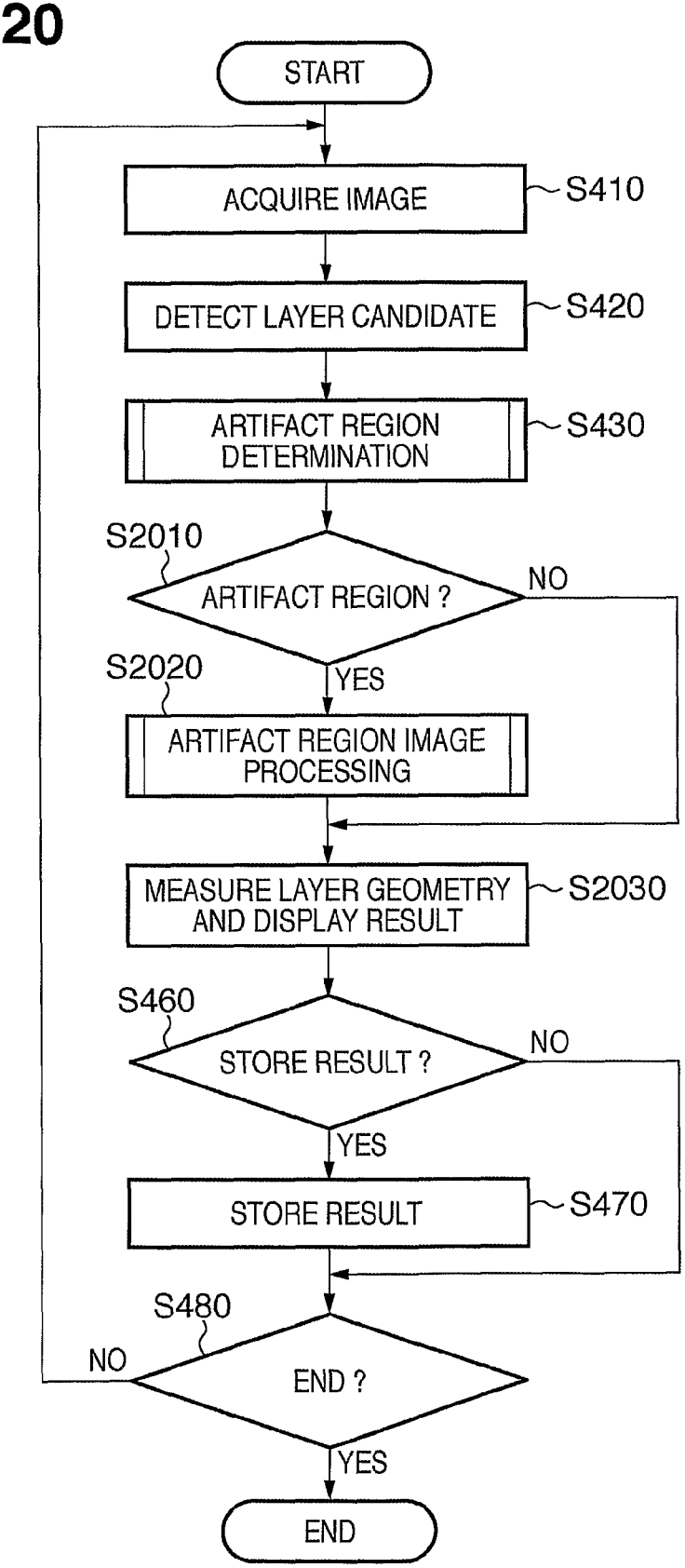
FIG. 20 is a flowchart showing the processing sequence of the image processing apparatus 10 according to the seventh embodiment.

The contents of image processing in this embodiment will be described below with reference to the image processing sequence shown in FIG. 20. Note that the image processing sequence of this embodiment is the same as that in the seventh embodiment except for the process in step S2020. Hence, change points of the process in step S2020 will be described below with reference to FIG. 24, and a description of other steps will not be repeated.

It is judged in step S2410 whether intensity information is used upon calculating a layer position since a weak edge remains in an artifact region or intensity information of, for example, an edge is not used since intensity is deficient. Since the practical judgment sequence is the same as that in step S2110 of the seventh embodiment, a description thereof will not be repeated.

In step S2420, a intensity use judgment unit 1911 branches processes according to the judgment result in step S2410. That is, if it is judged that intensity information in the artifact region is used upon deciding a layer position, the unit 1911 transmits a signal which instructs the image correction method setting unit 1913 to execute predetermined processing. On the other hand, if it is judged that intensity information in the region is not used, the unit 1911 transmits a signal which instructs the interpolation function setting unit 1914 to execute predetermined processing.

In step S2430, parameters required to execute conversion (image correction) of intensities in the artifact region are set. Various image correction methods are available. In this embodiment, setting sequences of parameters in the following image correction methods will be explained.

(i) Method based on linear conversion
(ii) Method based on histogram conversion
(iii) Method that emphasizes a layer structure Upon execution of image correction based on linear conversion in (i), using a maximum intensity $I_{maxF}$ in an artifact region, a minimum intensity $I_{minF}$ in the region, and a maximum intensity $I_{maxT}$ in a true image region, linear conversion parameters are set as follows:

$$y = I_{maxT} * (x - I_{minF})/I_{maxF} - I_{minF})$$

where y is a intensity in the artifact region after image correction, and x is a intensity in the artifact region before image correction. In this case, image correction which adjusts the maximum intensity in the artifact region to that in the true image region is executed.

In the method of (ii), various histogram conversions are executed to approximate histogram characteristics in an artifact region to those of a true image region. In this method, a intensity average and variance in the artifact region are adjusted to be the same as those in a true image region. In this case, using a standard deviation $S_f$ and average value $A_f$ of intensities in the artifact region and a standard deviation $S_t$ and average value $A_t$ of intensities in the entire image except for the artifact region, parameters of an image correction function can be set as follows:

$$y = (S_t/S_f) * (x - A_f) + A_t$$

where x is a signal before correction, and y is a signal after correction.

Furthermore, in the method of (iii), when layer structure emphasizing processing is executed using eigenvalues of a Hessian matrix, a conditional formula associated with the eigenvalues $\lambda_1, \lambda_2$, and $\lambda_3$ ($\lambda_2 \geq \lambda_2 \geq \lambda_3$) is described by formula (5) above. The Hessian matrix is a square matrix made by the entire second partial derivatives of a multi-variable function, as given by equation (3), and I is a density value of an image. From these three eigenvalues, the layer structure can be emphasized using equation (6) above. Note that $\omega(\lambda_s;\lambda_t)$ is a weight used for the layer structure emphasizing processing, and is set as in equation (7) above. However, in equation (7), a practical combination of values s and t is (s, t)=(1, 3) or (2, 3), and γ and α are respectively set to be fixed values.

In order to achieve the layer structure emphasizing processing according to the thickness of a layer to be detected, a smoothing parameter s based on a Gaussian function, which is executed as pre-processing of the layer structure emphasizing processing, is set as follows.

(i) From intensity profiles on A-scan lines at a layer position around an artifact region, a layer thickness at that layer position is calculated. In this case, a range on the lines in which differences from intensities at the layer position are equal to or smaller than a predetermined value is calculated, and its length is used as a layer thickness.

(ii) A value of a resolution s of a Gaussian filter used upon smoothing is set in proportion to a value of the layer thickness around the artifact region.

Note that the image correction methods in this embodiment are not limited to these methods. For example, arbitrary image correction methods may be used as long as a relationship of an increasing function is established between intensities before and after correction in the artifact region is established, and they include adjustable parameters.

In step S2440, the image correction unit 333 executes conversion (image correction) of intensities in the artifact region based on the image correction method set in step S2430, thus facilitating detection of the layer position. Furthermore, in step S2450 the layer decision unit 334 acquires image features of a layer to be extracted based on intensity information of the region which has undergone the image correction by the image correction unit 333, and defines a layer position by connecting these feature points. For example, a retinal pigment epithelium is originally a highest-intensity region on respective A-scan lines, and tends to have higher intensities even in the artifact region. Hence, the layer position is decided by connecting maximum intensity pixels located on the positive direction side of the z-axis of layer candidate points on respective A-scan lines in the image-corrected region in the x-axis direction.

With the above sequence, the layer position when the intensity use judgment unit 1911 judges that intensity information in the artifact region is used is decided. The processing contents of the image processing method decision unit 1910 when the intensity use judgment unit 1911 judges that intensity information in an artifact region is not used will be described below.

In step S2460, the image processing method decision unit 1910 acquires information associated with a range of an artifact region calculated by an artifact region determination unit 332. More specifically, letting i be a label of an artifact region in FIG. 25, the unit 1910 acquires information associated with a generation position $(x_i, y_i)$ and width $W_i$ of an artifact, and the number $d_i$ of layer candidate points which belong to a true image region $n_i$ near the region. In step S2470, the unit 1910 calculates an index which represents a degree of unevenness of a layer candidate point sequence, which exists around the artifact region. Since such index is the same as that calculated in step S2120, a detailed description thereof will not be repeated.

Furthermore, in step S2480 the image processing method decision unit 1910 selects a type or order of an interpolation function used upon interpolating layer candidate point sequences between artifact regions, and layer candidate points used in interpolation from the information acquired in steps S2460 and S2470.

(i) Initially, in each artifact region, a type or order of an interpolation function is selected from the width $W_i$ of the artifact region and a value (for example, a statistical amount of angles $\theta_i$ between layer candidate points) of the index associated with the layer geometry near the region calculated in step S2470. For example, if $W_i$ is less than a predetermined value, linear interpolation is selected; if it is equal to or larger than the predetermined value, B-spline interpolation is selected. Alternatively, the following selection method may be used. That is, if the layer geometry has a large unevenness (if an average or maximum value of $\theta_i$ is equal to or larger than a predetermined value), natural spline interpolation whose interpolation curve passes through control points and which allows to calculate a more precise layer position than B-spline interpolation is used. Also, the following selection method may be used. That is, even for the interpolation function of the same type, an order of the interpolation function is set in proportion to the magnitude of the statistical amount (average value, maximum value, etc.) of angles $\theta_i$ between layer candidate points around the artifact region.

(ii) Then, layer candidate points used in interpolation of a layer position in the artifact region are selected. More specifically, it is checked if the numbers $d_{i-1}$ and $d_i$ of layer candidate points which belong to true image regions and $n_i$ near an artifact region i satisfy the minimum required number required to perform interpolation by the selected interpolation function. If these numbers satisfy the minimum required number, layer candidate points near the artifact region of those which belong to these true image regions are selected by the number required for interpolation. On the other hand, if these numbers do not satisfy the minimum required number, layer candidate points which belong to another true image region are selected. For example, when the number of layer candidate points which exist in a true image region (for example, a true image region $n_{i+1}$ in FIG. 25) does not suffice to be used in interpolation, layer candidate points in a neighboring region $n_{i+2}$ are further selected.

Figure 25:
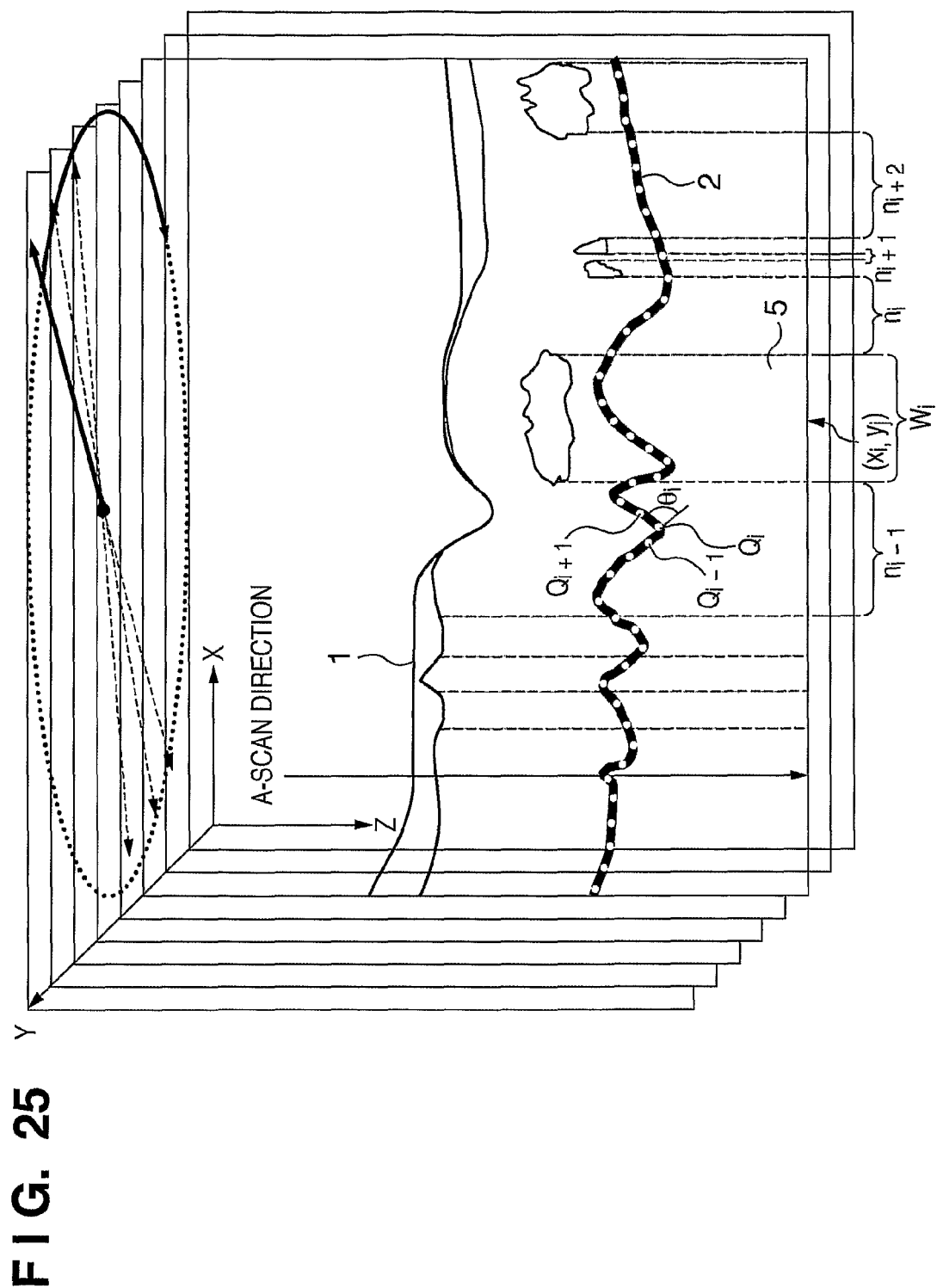
FIG. 25 is a view for explaining an image processing method decision method and layer decision method according to the eighth embodiment.

When true image regions having the sufficient numbers of layer candidate points do not exist in a direction to be currently interpolated (for example, when an artifact region exists at the edge of an image region), layer candidate points are selected as follows. That is, the direction to be interpolated is changed to a direction in which layer candidate points that can be used in interpolation sufficiently exist, and layer candidate points which belong to true image regions near that direction are selected. For example, when an artifact region exists at the edge of an image, as shown in FIG. 25, and the number of layer candidate points used in interpolation in association with an x-direction is short, layer candidate points in true image regions, which exist near the artifact region on a y-z plane that passes through the artifact region, can be selected. Note that the type of direction to be interpolated is not always limited to a direction parallel to the x- or y-axis, and it may be changed to an arbitrary direction in which layer candidate points that can be used in interpolation sufficiently exist. For example, in consideration of the fact that a layer geometry tends to have image features similar to a concentric shape in, for example, a macula portion or optic papilla, layer candidate points in true image regions, which exist near an artifact region on a plane generated by circular scan like in FIG. 25, may be selected. Information associated with the image processing method decided in this step is transmitted to the layer decision unit 334.

In step S2450, the layer decision unit 334 decides the layer position in the artifact region by interpolating between layer candidate points selected in step S2480 by the interpolation function of the type selected in that step. Then, information of the calculated layer position is output to a storage unit 320.

With the above sequence, the artifact region image processing corresponding to this embodiment is executed. Note that in this embodiment, image correction is executed after the image processing method is decided. However, the image correction execution timing is not limited to this. For example, after the processing by the artifact region determination unit 332, the image correction unit 333 may execute image correction according to the degree of intensity attenuation in the region. In this case, the image processing method decision unit receives the image correction result, and makes settings associated with interpolation processing in response to the judgment result by the intensity use judgment unit.

Also, the image correction method setting unit 1913 is included in the image correction unit 333.

According to the aforementioned arrangement, the image processing apparatus 10 specifies an artifact region, and judges whether or not to use intensity information of, for example, an edge in the artifact region. If intensity information of, for example, an edge is used, the layer decision processing is executed after intensities in the region are corrected. When the information is not used, interpolation processing is executed according to a range of the artifact region and the layer geometry around the region, thus calculating a layer position with high precision.

Ninth Embodiment

In this embodiment, a projection image is generated from a tomogram of an eye to be examined, and position information of tissue or a morbid portion extracted from the projection image is back-projected onto the tomogram to narrow down artifact candidate regions, in place of calculating a layer position in an artifact region using only a tomogram in the seventh embodiment.

This embodiment covers the following points.

(i) Position information of a blood vessel (bleeding) region calculated from a projection image is mapped onto a tomogram, and an edge portion of an artifact region is searched for and specified from a surrounding region of the mapped region, thus allowing to calculate a range of the artifact region with higher precision.

(ii) Since a layer model is applied by weighting evaluation functions in consideration of edge information remaining in an artifact region and an unevenness of a layer geometry around the artifact region, a more precise layer position can be calculated.

Figure 26:
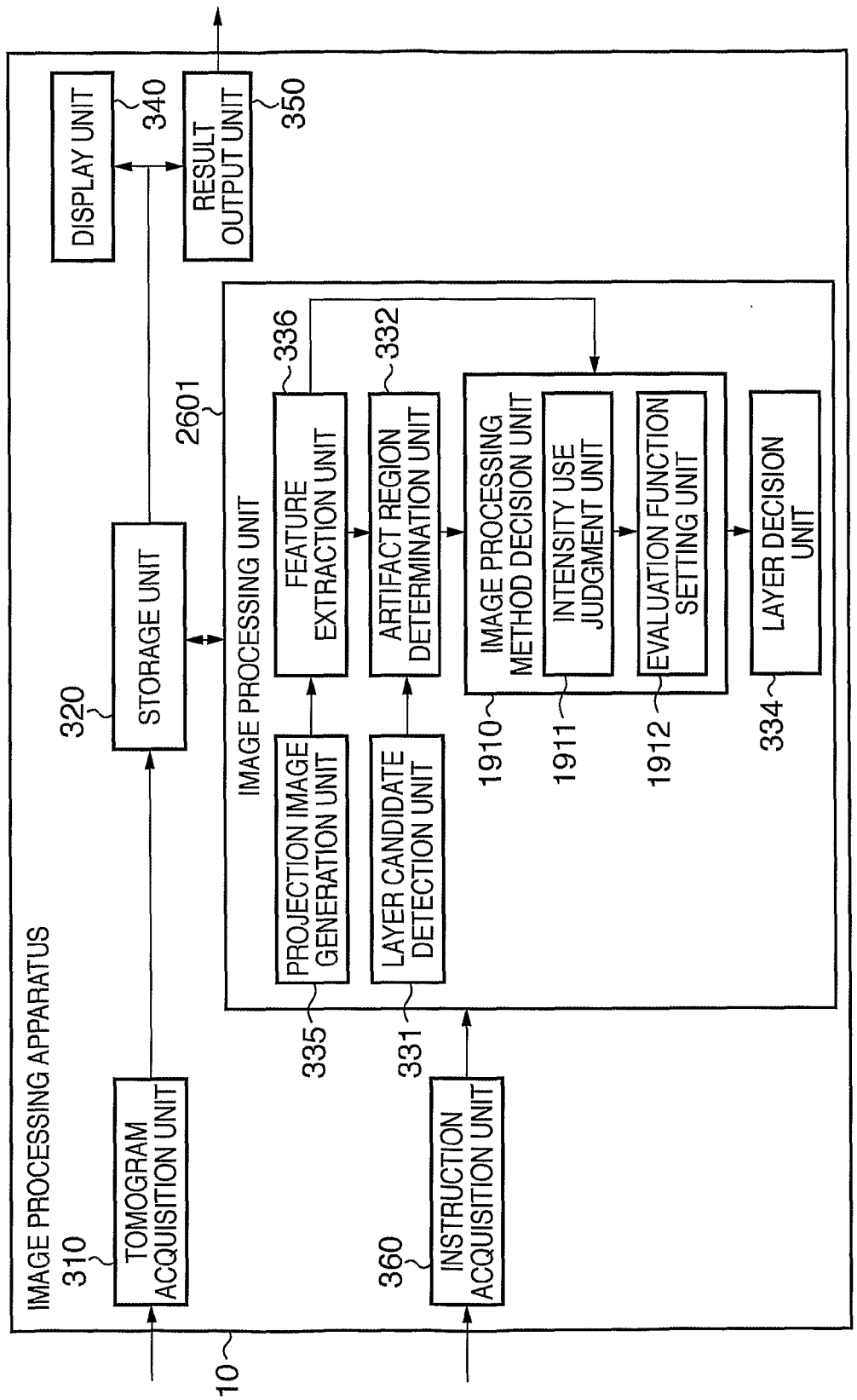
FIG. 26 is a block diagram showing the functional arrangement of an image processing apparatus 10 according to the ninth embodiment.

Since the arrangement of apparatus connected to an image processing apparatus 10 according to this embodiment is the same as that of the seventh embodiment, a description thereof will not be given. FIG. 26 is a functional block diagram of the image processing apparatus 10 according to this embodiment. An image processing unit 2601 of this embodiment includes a projection image generation unit 335 and feature extraction unit 336 unlike in the image processing unit 1901 shown in FIG. 19 of the seventh embodiment. Since the remaining units are the same as those in FIG. 19, a description thereof will not be repeated.

Figure 27:
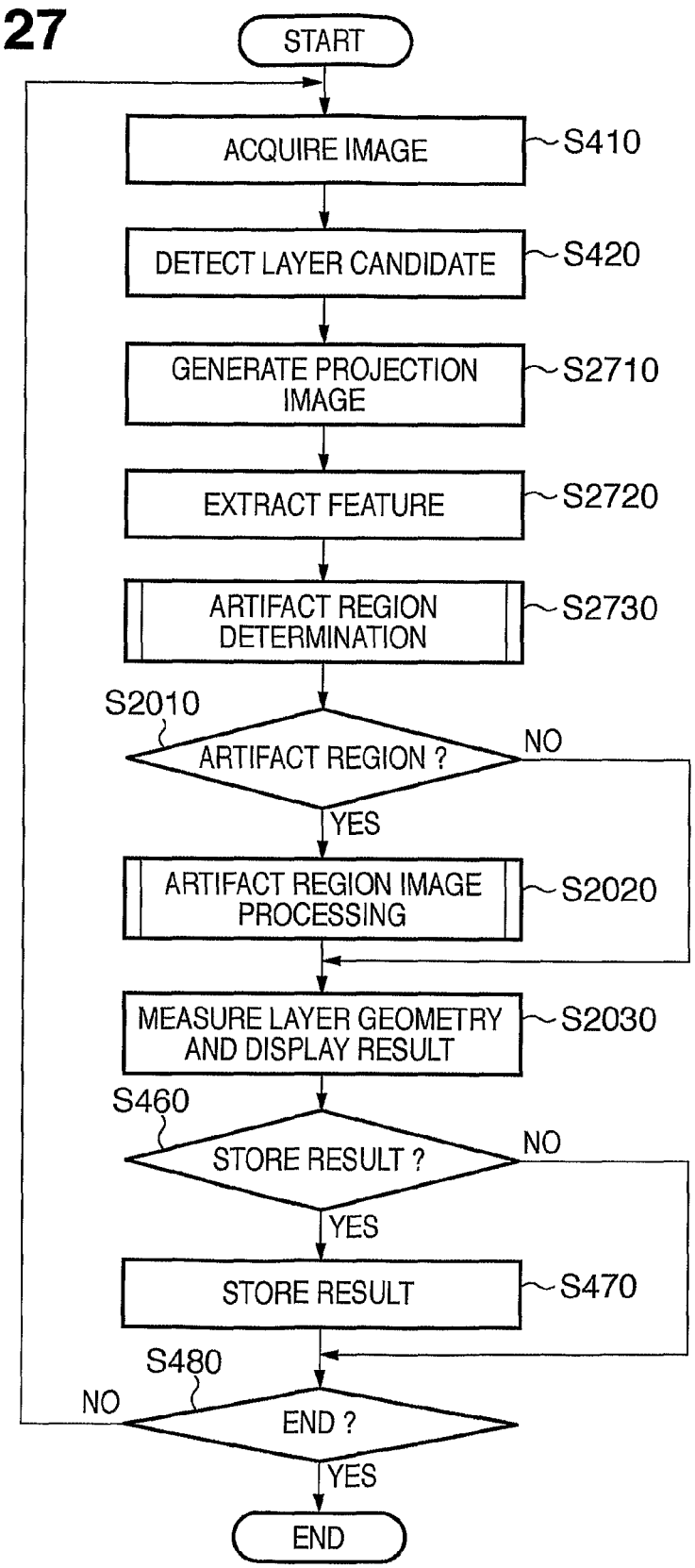
FIG. 27 is a flowchart showing the processing sequence of the image processing apparatus 10 according to the ninth embodiment.

The contents of image processing of this embodiment will be described below with reference to the image processing sequence shown in FIG. 27. Note that the processing of this embodiment is the same as that shown in FIG. 20 of the seventh embodiment, except for processes in steps S2710, S2720, and S2730. Hence, the processes in steps S2710, S2720, and S2730 will be described below.

In step S2710, the projection image generation unit 335 generates an image by projecting a tomogram. Since a practical generation method is the same as that described in step S1110 in FIG. 11 of the third embodiment, a description thereof will not be repeated. In step S2720, features of tissue such as a retina blood vessel or a morbid portion are extracted from the projection image generated by the projection image generation unit 335. Since a practical generation method is the same as that described in step S1120 in FIG. 11 of the third embodiment, a description thereof will not be repeated.

Figure 28:
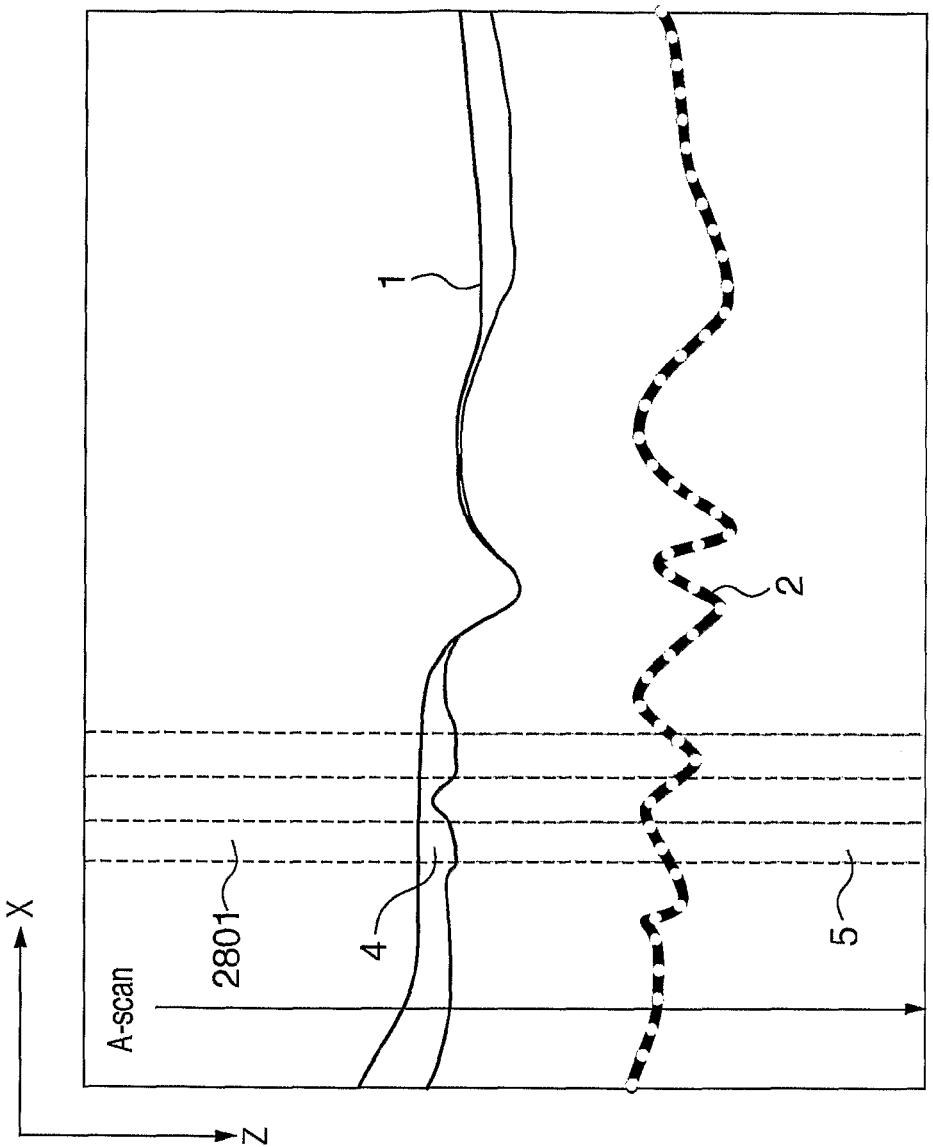
FIG. 28 is a view for explaining an artifact region determination method according to the ninth embodiment.

In step S2730, when a blood vessel region (x, y) on the projection image calculated in step S2720 is back-projected onto the tomogram, a region indicated by a dotted region 2801 in FIG. 28 (to be referred to as a back-projection region hereinafter) is obtained. In general, on the positive direction side of a z-axis of a retina blood vessel, attenuation of intensities readily occurs. Therefore, when the position (in x-y directions) of the extracted feature is back-projected onto the tomogram, the back-projected dotted region 2801 is more likely to include an artifact region 5. However, when an erroneously extracted region is back-projected, no intensity attenuation occurs in the back-projection region. Even when a correctly extracted retina blood vessel region is back-projected, intensity attenuation below the back-projection region is slight and has nearly no influence on layer extraction in some cases. Hence, whether or not an artifact is generated in the back-projection region and near the boundary of that region is determined. If an artifact region is generated, a statistical amount associated with intensities in that region is calculated.

The artifact region determination method is basically the same as that in steps S610 to S640 of the first embodiment, except for a range of layer candidate points as calculation targets of a continuity. More specifically, the continuity calculation processing is executed not for all layer candidate points, but for the interior of the back-projection region and in the vicinity of the region in x-y directions.

According to the aforementioned arrangement, an artifact region is specified using a tomogram and projection image, and a layer model is applied by weighting evaluation functions in consideration of not only a layer geometry around the region but also edge information in the region, thus calculating a layer position with high precision.

10th Embodiment

This embodiment executes image correction of an artifact region and then calculates a layer position when intensity information of, for example, an edge is used after judgment of a intensity use judgment unit, and calculates a layer position by interpolation processing when the information is not used, in the ninth embodiment.

This embodiment covers the following points.

(i) Position information of a blood vessel (bleeding) region calculated from a projection image is mapped onto a tomogram, and an edge portion of an artifact region is searched for and specified from a surrounding region of the mapped region, thus allowing to calculate a range of the artifact region with higher precision.

(ii) In, for example, a blood vessel region where information of an attenuated edge remains, a layer position is detected after intensities are converted, thus calculating the layer position more precisely.

(iii) In a region where intensities are deficient and intensity information of, for example, an edge cannot be used, surrounding layer positions are interpolated in consideration of the generation position of an artifact region and a surrounding layer geometry, thus calculating the layer position more precisely.

Figure 29:
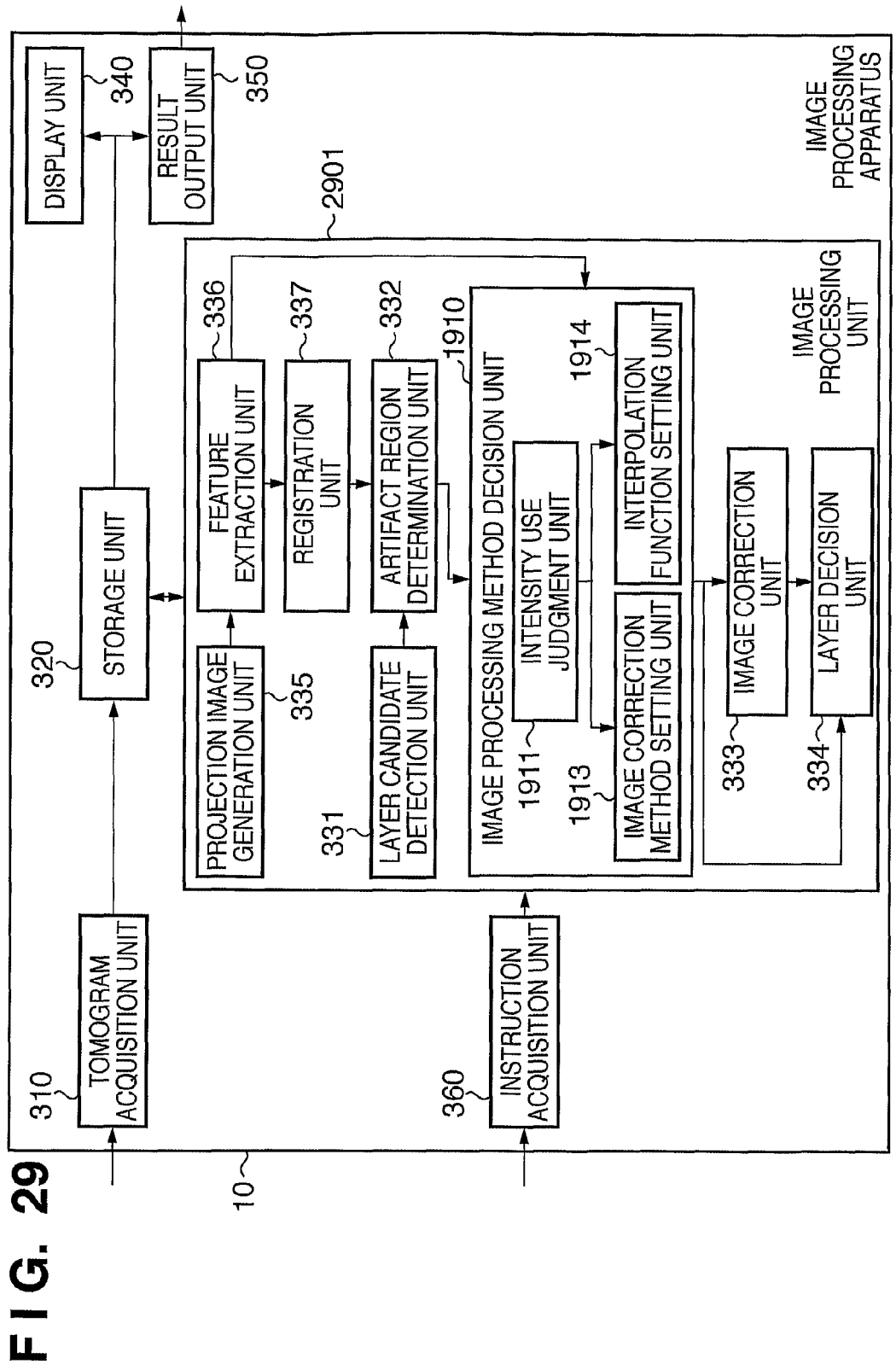
FIG. 29 is a block diagram showing the functional arrangement of an image processing apparatus 10 according to the 10th embodiment.

Since the arrangement of apparatus connected to an image processing apparatus 10 according to this embodiment is the same as that in the ninth embodiment, a description thereof will not be repeated. FIG. 29 is a functional block diagram of the image processing apparatus 10 according to this embodiment. An image processing unit 2901 of this embodiment further includes a registration unit 337, and an image processing method decision unit 1910 includes an image correction method setting unit 1913 and interpolation function setting unit 1914 in place of the evaluation function setting unit 1912 unlike in the ninth embodiment. The contents of image processing of this embodiment will be described below with reference to the image processing sequences shown in FIGS. 24 and 27. Note that processes other than step S2020 are the same as those in the ninth embodiment. Hence, the process in step S2020 will be described below, and a description of other steps will not be repeated.

In step S2020, image processing in an artifact region is executed. Since the processing in this step is the same as that in steps S2410 to S2480 of FIG. 24 in the eighth embodiment, a detailed description thereof will not be repeated.

According to the aforementioned arrangement, the image processing apparatus 10 specifies an artifact region using a tomogram and projection image, and judges whether or not to use intensity information of, for example, an edge in the region. When the information is used, layer determination processing is executed after intensities in the region are corrected. When the information is not used, interpolation processing is executed according to a range of the artifact region and the layer geometry around the region, thus calculating a layer position with high precision.

11th Embodiment

This embodiment adds, to the ninth embodiment, processing for back-projecting, onto a tomogram, position information of tissue or a morbid portion extracted from at least one of a surface image of an eye to be examined and a projection image so as to narrow down artifact candidate regions in advance.

This embodiment covers the following points.

(i) When a morbid portion such as an exudate, which can be easily extracted from a surface image, is generated, an exudate region is extracted from the surface image, its position information is mapped onto a tomogram, and an edge portion of an artifact region is searched for and specified from a surrounding region of that region, thus calculating a range of an artifact region with higher precision.

(ii) Since a layer model is applied by weighting evaluation functions in consideration of edge information remaining in an artifact region and an unevenness of a layer geometry around the artifact region, a more precise layer position can be calculated.

Figure 30:
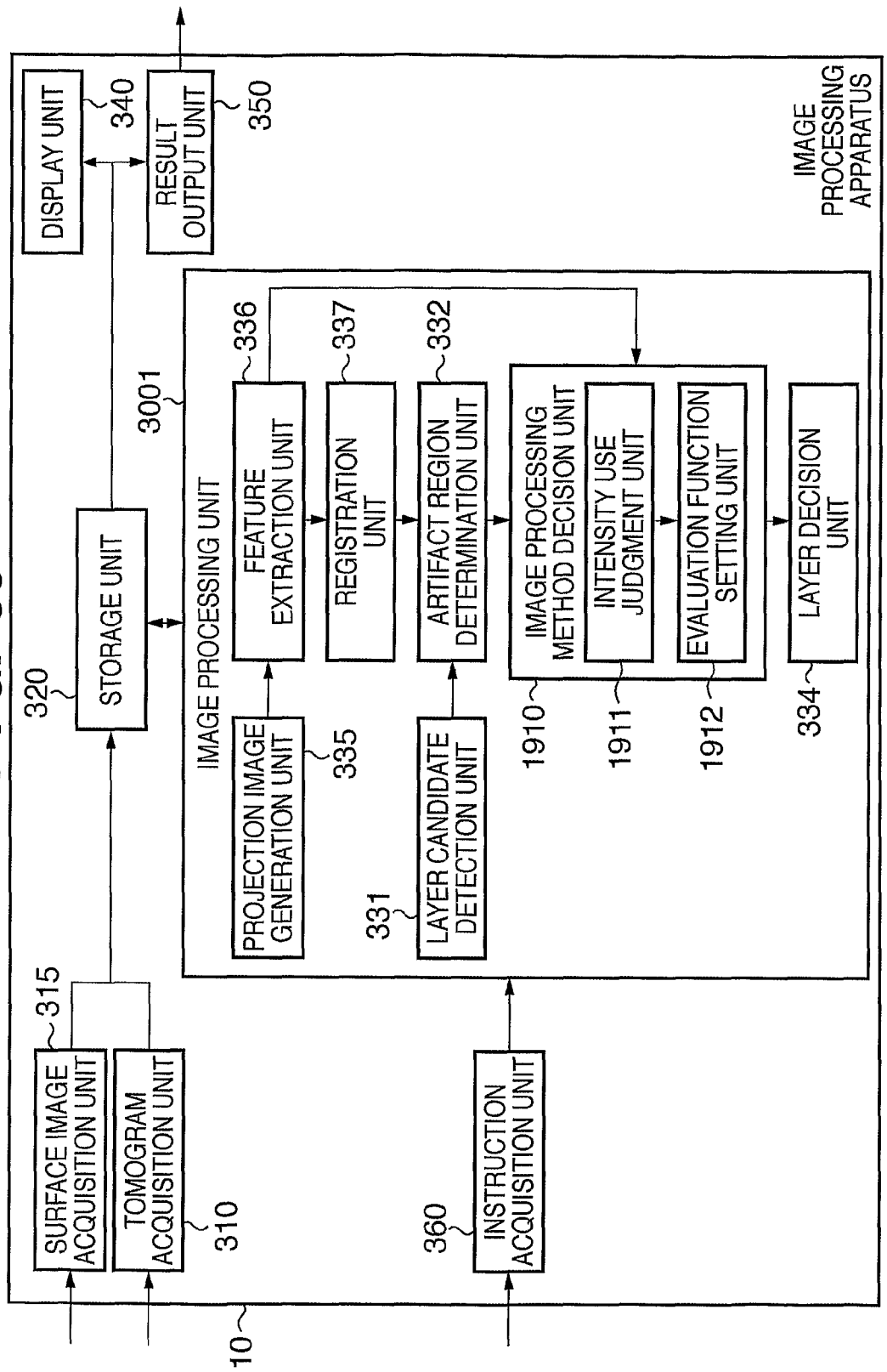
FIG. 30 is a block diagram showing the functional arrangement of an image processing apparatus 10 according to the 11th embodiment.

The arrangement of apparatus connected to an image processing apparatus 10 according to this embodiment additionally includes a surface image capturing apparatus 50, as shown in FIG. 14, unlike in the ninth embodiment. Also, in the image processing apparatus 10 according to this embodiment, an image processing unit 3001 includes a surface image acquisition unit 315, as shown in FIG. 30, unlike in the ninth embodiment.

Figure 31:
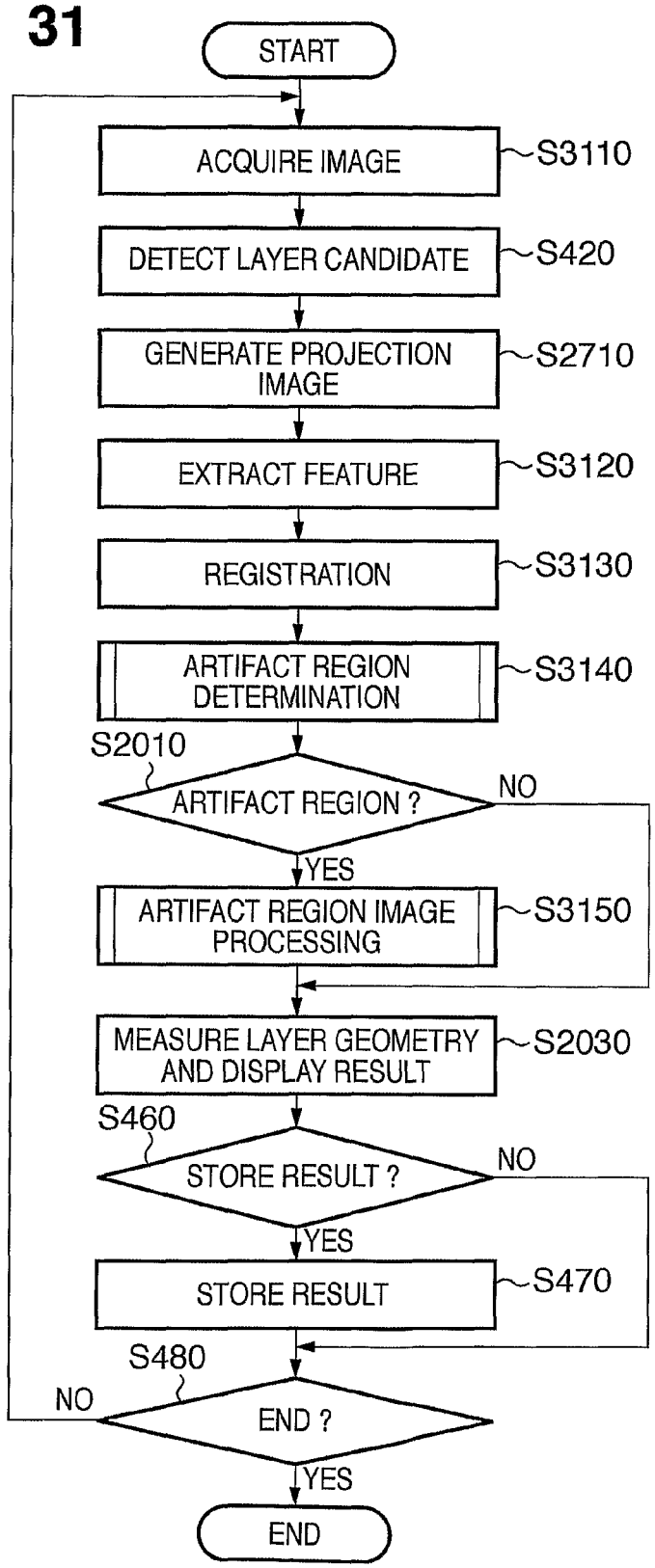
FIG. 31 is a flowchart showing the processing sequence of the image processing apparatus 10 according to the 11th embodiment.

The contents of image processing of this embodiment will be described below with reference to the image processing sequence shown in FIG. 31. Note that since the processes other than those in steps S3110 to S3150 are the same as those in the ninth embodiment, a description thereof will not be repeated. Also, the processes in steps S3110 to S3140 are the same as those in steps S1610 to S1640 of the aforementioned fifth embodiment, and a description thereof will not be repeated.

Furthermore, in step S3150 image processing in an artifact region is executed. The processing in this step is basically the same as that in steps S2110 to S2140 of the seventh embodiment. However, in this embodiment, in step S2130, image processing parameters may be set also using information obtained from a fundus image. For example, when intensities of an exudate are very high on a fundus image, since intensities are more likely to be attenuated on the positive direction side of a z-axis of an exudate region also on a tomogram, weights of evaluation functions associated with a geometry are increased in proportion to intensity signal values of the exudate region. As the intensity signal values of the exudate region, pixel values of that region on the fundus image may be directly referred to, or values (multi-valued data) of a region obtained as the processing result of morphology operations or the like may be referred to.

According to the aforementioned arrangement, in an artifact region specified using a surface image and projection image, since a layer model is applied by weighting evaluation functions in consideration of not only the layer geometry around the region but also intensity information in the region, thus calculating a layer position with high precision.

12th Embodiment

This embodiment executes image correction of an artifact region and then decides a layer position when intensity information of, for example, an edge is used after judgment of a intensity use judgment unit, and calculates a layer position by interpolation processing when the information is not used, in the 11th embodiment.

This embodiment covers the following points particularly when an artifact is generated by an exudate.

(i) Position information of an exudate region calculated from a surface image is mapped onto a tomogram, and an edge portion of an artifact region is searched for and specified from a surrounding region of the mapped region, thus allowing to calculate a range of the artifact region with higher precision.

(ii) In, for example, a blood vessel region where information of an attenuated edge remains, a layer position is detected after intensities are converted, thus calculating the layer position more precisely.

(iii) In a region where intensities are omitted and intensity information of, for example, an edge cannot be used, surrounding layer positions are interpolated in consideration of the generation position of an artifact region and a surrounding layer geometry, thus calculating the layer position more precisely.

Figure 32:
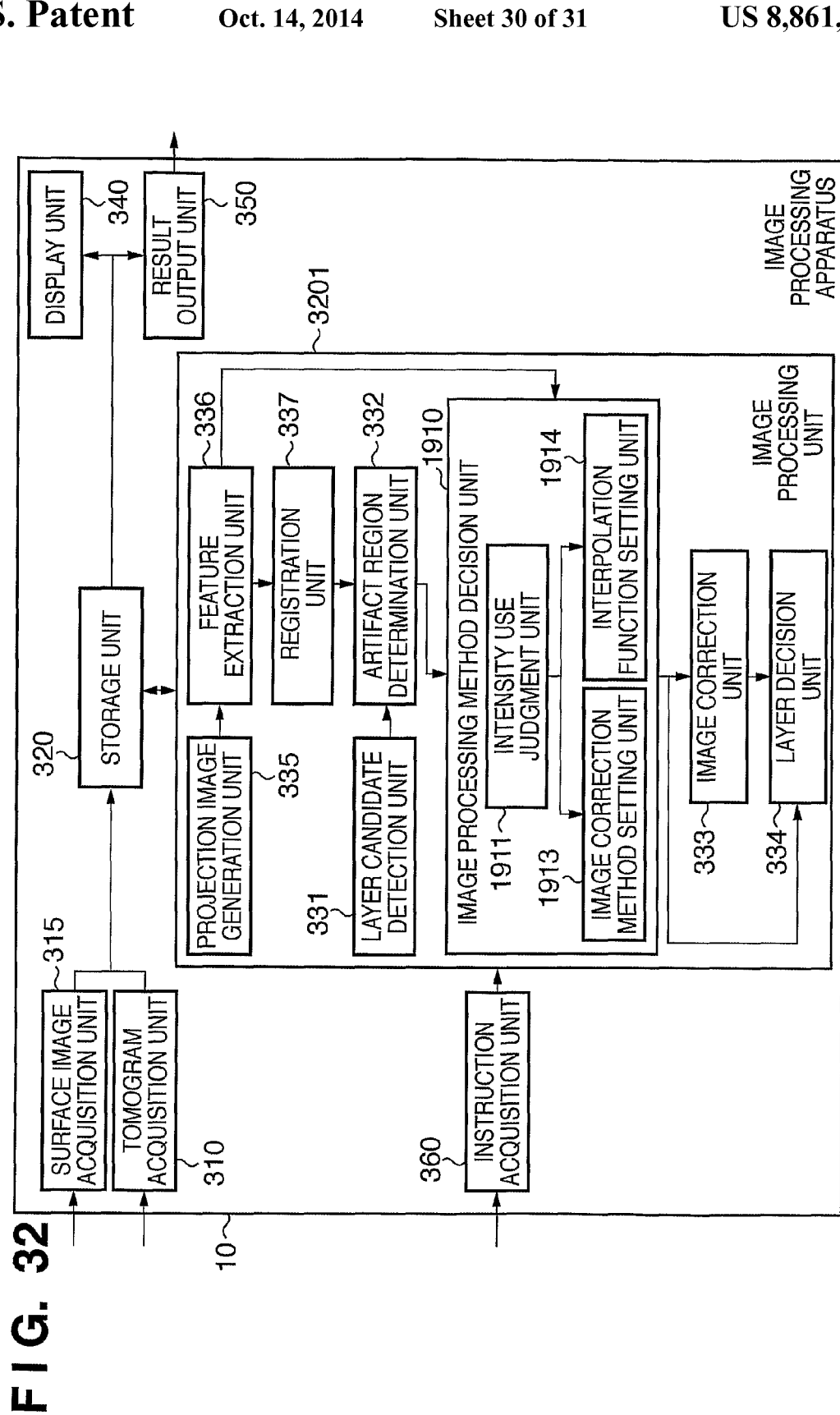
FIG. 32 is a block diagram showing the functional arrangement of an image processing apparatus 10 according to the 12th embodiment.

Since the arrangement of apparatus connected to an image processing apparatus 10 according to this embodiment is the same as that in the 11th embodiment, a description thereof will not be repeated. FIG. 32 is a functional block diagram of the image processing apparatus 10 according to this embodiment. In this embodiment, an image processing method decision unit 1910 includes an image correction method setting unit 1913 and interpolation function setting unit 1914 in place of the evaluation function setting unit 1912 unlike in the fifth embodiment. Also, the image processing sequence in this embodiment is basically the same as that in the 11th embodiment. However, the processing in step S3150 is executed as follows.

Figure 24:
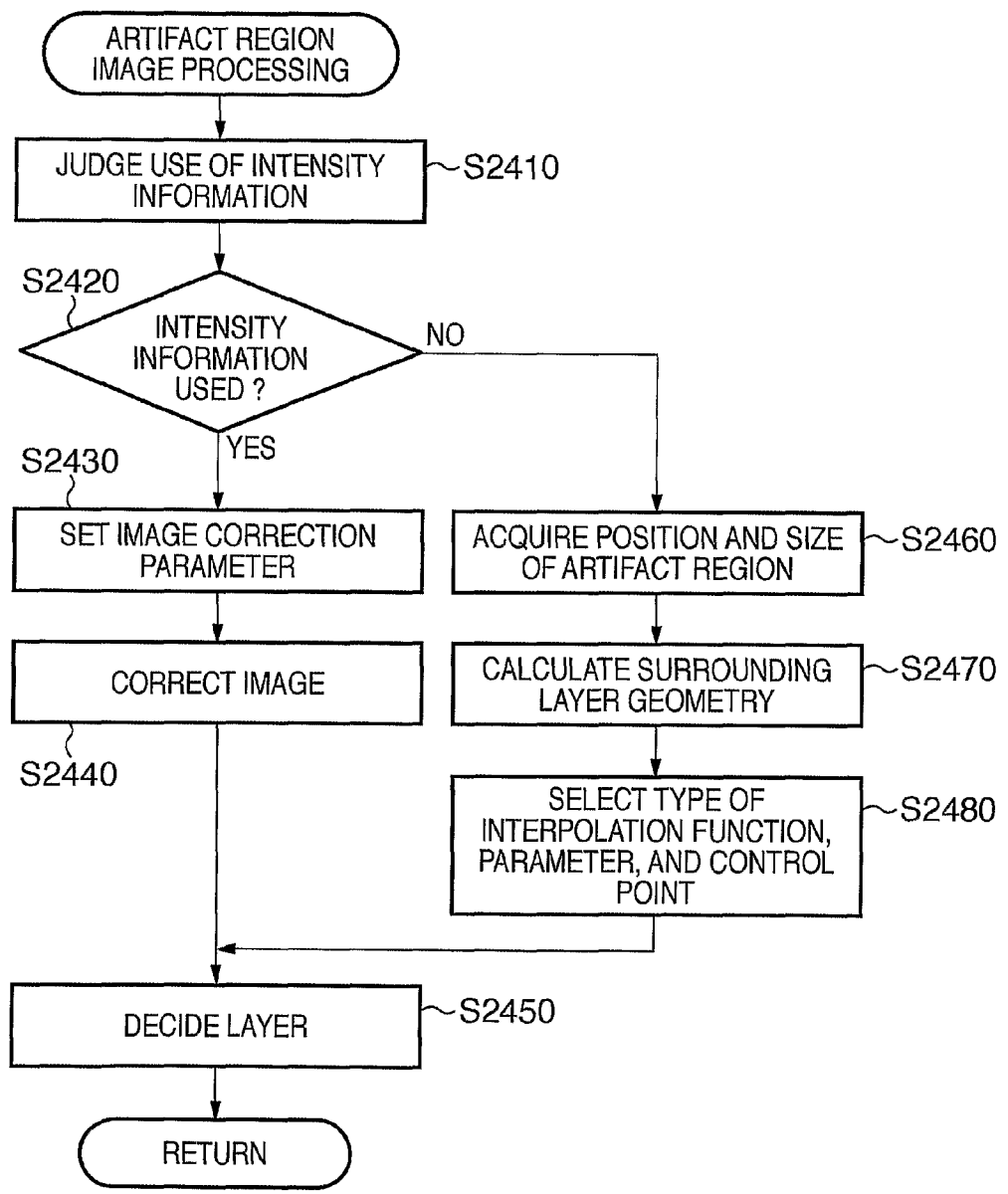
FIG. 24 is a flowchart showing the image processing sequence for a region determined as an artifact region according to the eighth embodiment.

However, the processing executed in step S3150 has the same sequence as in the 10th embodiment. That is, whether or not to use intensity information of, for example, an edge in an artifact region is judged, as shown in FIG. 24. When the information is used, layer decision processing is executed after intensities in the region are corrected. When the information is not used, a type of an interpolation function and parameters are set according to a range of the region and the layer geometry around the region, and interpolation processing is then executed.

According to the aforementioned arrangement, in an artifact region specified using a surface image and projection image, whether or not to use intensity information of, for example, an edge in that region is judged. When the information is used, layer decision processing is executed after intensities in the region are corrected. When the information is not used, interpolation processing is executed according to a range of the artifact region and the layer geometry around the region. In this way, a layer position can be calculated with high precision.

Other Embodiments

The aforementioned embodiments implement the present invention as an image processing apparatus. However, an embodiment of the present invention is not limited to only the image processing apparatus, but may be implemented as software which implements functions when it is executed by a CPU of a computer.

Figure 33:
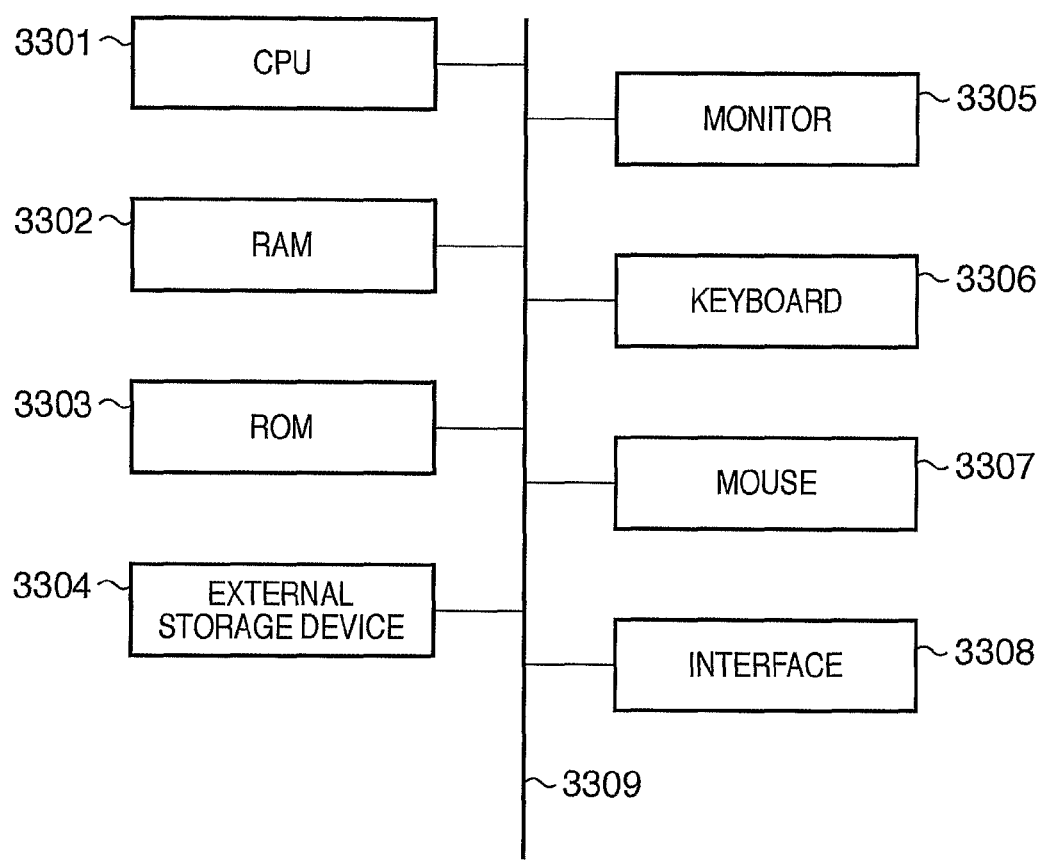
FIG. 33 is a block diagram showing the basic arrangement of a computer that can implement respective units of the image processing apparatus 10 by software.

FIG. 33 is a block diagram showing the basic arrangement of a computer used to implement the functions of respective units of an image processing apparatus 10 as software. A CPU 3301 controls the overall computer using programs and data stored in a RAM 3302 and ROM 3303. Also, the CPU 3301 implements the functions of the respective units by controlling execution of software programs corresponding to the respective units of the image processing apparatus 10. The RAM 3302 includes an area for temporarily storing computer programs and data loaded from an external storage device 3304, and also a work area required for the CPU 3301 to execute various processes. The function of a storage unit 320 is implemented by the RAM 3302.

The ROM 3303 generally stores a BIOS, setting data, and the like of the computer. The external storage device 3304 serves as a large-capacity information storage device such as a hard disk drive, and stores an operating system and programs executed by the CPU 3301. The external storage device 3304 stores information which is given in the description of this embodiment, and such information is loaded onto the RAM 3302 as needed. A monitor 3305 is configured by, for example, a liquid crystal display. For example, the monitor 3305 can display the contents output from a display unit 340.

A keyboard 3306 and mouse 3307 are input devices. An operator can input various instructions to the image processing apparatus 10 using these input devices. An interface 3308 is used to exchange various data between the image processing apparatus 10 and external apparatus, and is configured by, for example, an IEEE1394, USB, or Ethernet® port. Data acquired via the interface 3308 is fetched onto the RAM 3302. Functions of a tomogram acquisition unit 310 and result output unit 350 are implemented via the interface 3308. The aforementioned components are interconnected via a bus 3309.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-133455, filed Jun. 2, 2009, which is hereby incorporated by reference herein in its entirety.

The invention claimed is:

1. An image processing apparatus, which processes an image of a tomogram obtained by capturing an image of an eye to be examined by a tomography apparatus, comprising:
a layer candidate detection unit configured to detect layer candidates of a retina of the eye to be examined from the tomogram;
an artifact region determination unit configured to determine an artifact region in the tomogram based on image features obtained using the layer candidates; and
an image correction unit configured to correct intensities in the artifact region based on a determination result of said artifact region determination unit and image features in the region.

2. The apparatus according to claim 1, further comprising a layer decision unit configured to decide a position of a layer of the retina in the artifact region, based on intensities in the artifact region, which are corrected by said image correction unit.

3. The apparatus according to claim 2, further comprising an intensity use judgment unit configured to judge, based on magnitudes of the intensities, whether or not to use the intensities in the artifact region in deciding the position of the layer,
wherein when said intensity use judgment unit judges that the intensities are used, said layer decision unit executes decision processing of the position of the layer using the intensities, and
when said intensity use judgment unit judges that the intensities are not used, said layer decision unit decides the position of the layer by interpolation processing using the layer candidates near the artifact region.

4. An image processing apparatus, which processes an image of a tomogram obtained by capturing an image of an eye to be examined by a tomography apparatus, comprising:
a layer candidate detection unit configured to detect layer candidates of a retina of the eye to be examined from the tomogram;
an artifact region determination unit configured to determine an artifact region in the tomogram based on image features obtained using the layer candidates; and
a layer decision unit configured to decide a position of a layer of the retina in the artifact region, based on a determination result of said artifact region determination unit,
wherein said layer decision unit uses a geometric model which is used to specify a layer geometry included in the artifact region and is defined by a plurality of control points, and decides the position of the layer based on evaluation functions associated with a geometry of the geometric model and evaluation functions associated with intensities near the control points.

5. The apparatus according to claim 4, wherein said layer decision unit decides weights of evaluation functions associated with intensities to increase the weights of the evaluation functions associated with the intensities with decreasing intensities of pixels in the artifact region, or decides weights of the evaluation functions in accordance with a ratio between intensities of pixels in the artifact region and intensities of pixels other than the artifact region in the tomogram, and
wherein said layer decision unit decides weights of the evaluation functions associated with the geometry so as to reduce the weights with increasing degree of unevenness in accordance with the degree of unevenness of a geometry of a layer specified by the layer candidates near the artifact region.

6. The apparatus according to claim 1, wherein the image features obtained using the layer candidates include a continuity between the layer candidates, and
wherein said artifact region determination unit determines the artifact region in the tomogram to have a layer candidate, which has a low continuity and is determined to be discontinuous, as an edge point of the artifact region.

7. The apparatus according to claim 6, wherein said artifact region determination unit uses, as the edge point of the artifact region, a layer candidate having lower intensities in a region deeper than respective layer candidates of two layer candidates which are determined to be discontinuous.

8. The apparatus according to claim 1, wherein the image features obtained using the layer candidates include differences between intensities of pixels in regions specified by the two layer candidates in a direction perpendicular to an A-scan direction of the tomogram, and
wherein said artifact region determination unit determines the artifact region in the tomogram based on a degree of difference between a plurality of intensity profiles in the A-scan direction.

9. The apparatus according to claim 1, further comprising:
a projection image generation unit configured to generate a projection image by adding respective pixels of the tomogram in an A-scan direction of the tomogram corresponding to a depth direction of the retina; and
a feature extraction unit for extracting a feature region including at least one of biological tissue and a morbid portion in the eye to be examined from the projection image,
wherein said artifact region determination unit determines the artifact region in and in the vicinity of the feature region.

10. The apparatus according to claim 9, wherein said feature extraction unit further extracts the feature region from a surface image obtained by capturing an image of the eye to be examined, and
wherein said artifact region determination unit determines the artifact region by further using the feature region extracted from the surface image.

11. A control method of an image processing apparatus, which processes an image of a tomogram obtained by capturing an image of an eye to be examined by a tomography apparatus, comprising:
a layer candidate detection step of controlling layer candidate detection unit to detect layer candidates of a retina of the eye to be examined from the tomogram;
an artifact region determination step of controlling artifact region determination unit to determine an artifact region in the tomogram based on image features obtained using the layer candidates; and
an image correction step of controlling image correction unit to correct intensities in the artifact region based on a determination result in the artifact region determination step and image features in the region.

12. A control method of an image processing apparatus, which processes an image of a tomogram obtained by capturing an image of an eye to be examined by a tomography apparatus, comprising:
a layer candidate detection step of controlling layer candidate detection unit to detect layer candidates of a retina of the eye to be examined from the tomogram;

an artifact region determination step of controlling artifact region determination unit to determine an artifact region in the tomogram based on image features obtained using the layer candidates; and a layer decision step of controlling layer decision unit to decide a position of a layer of the retina in the artifact region, based on a determination result in the artifact region determination step, wherein in the layer decision step, a geometric model which is used to specify a layer geometry included in the artifact region and is defined by a plurality of control points is used, and the position of the layer is decided based on evaluation functions associated with a geometry of the geometric model and evaluation functions associated with intensities near the control points.

13. A non-transitory computer-readable storage medium storing a computer program for making a computer function as respective units of an image processing apparatus which processes an image of a tomogram obtained by capturing an image of an eye to be examined by a tomography apparatus, said image processing apparatus comprising:

a layer candidate detection unit configured to detect layer candidates of a retina of the eye to be examined from the tomogram;

an artifact region determination unit configured to determining an artifact region in the tomogram based on image features obtained using the layer candidates; and an image correction unit configured to correct intensities in the artifact region based on a determination result of said artifact region determination unit and image features in the region.

14. A non-transitory computer-readable storage medium storing a computer program for making a computer function as respective units of an image processing apparatus which processes an image of a tomogram obtained by capturing an image of an eye to be examined by a tomography apparatus, said image processing apparatus comprising:

a layer candidate detection unit configured to detect layer candidates of a retina of the eye to be examined from the tomogram;

an artifact region determination unit configured to determine an artifact region in the tomogram based on image features obtained using the layer candidates; and a layer decision unit configured to decide a position of a layer of the retina in the artifact region, based on a determination result of said artifact region determination unit, wherein said layer decision unit uses a geometric model which is used to specify a layer geometry included in the artifact region and is defined by a plurality of control points, and decides the position of the layer based on evaluation functions associated with a geometry of the geometric model and evaluation functions associated with intensities near the control points.

15. A method for processing an image of a tomogram obtained by capturing an image of an eye to be examined by a tomography apparatus, comprising:

an identifying step for identifying an artifact region in the tomogram;

a first detection step for detecting, by a first method, boundaries of layers constituting a retina of the eye to be examined in a region other than the artifact region;

a second detection step for detecting, by a second method different from the first method based on an intensity of the artifact region, boundaries of layers constituting the retina of the eye to be examined in the artifact region of the tomogram; and a display step for displaying lines indicating the detected boundaries of the layers by superimposing them on the tomogram.

16. The method according to claim 15, wherein the first method is different from the second method with respect to an algorithm to be used to detect the layers and/or a threshold to be used to detect the boundaries of the layers.

17. The method according to claim 15, wherein in said second detection step, the boundaries of the layers in the artifact region are detected based on the intensity of the artifact region and positions of the boundaries of the layers detected by the first method.

18. The method according to claim 15, wherein in said identifying step, a blood vessel region and/or an exudates region is extracted using the tomogram and/or a fundus image of the eye to be examined and, a region corresponding to the extracted region in the tomogram is identified as the artifact region.

19. The method according to claim 15, wherein in said identifying step, it is determined whether the artifact region having an attenuated intensity exists or not in a region of the tomogram corresponding to the blood vessel region or the exudates region.

20. The method according to claim 15, wherein in said identifying step, the artifact region is identified based on a continuity of candidate points of a predetermined layer boundary detected in the tomogram.

21. The method according to claim 15, wherein in said identifying step, a region, located on the rear side of a blood vessel region of the retina when viewed from the front side of the eye to be examined, is identified as the artifact region.

22. An image processing apparatus which performs a method according to claim 15, the apparatus comprising:

identifying means for performing said identifying step;

detection means for performing said first detection step and said second detection step; and display means for performing said display step.

23. A tomography system comprising:

an image processing apparatus according to claim 22; and a tomography apparatus.

24. An image processing apparatus for processing an image of a tomogram obtained by capturing an image of an eye to be examined by a tomography apparatus, comprising:

an identifying means for identifying an artifact region in the tomogram;

a detection means for detecting, by a first method, boundaries of layers constituting a retina of the eye to be examined in a region other than the artifact region based on an intensity of the region other than the artifact region, and for detecting, by a second method different from the first method based on an intensity of the artifact region, boundaries of layers constituting the retina of the eye to be examined in the artifact region of the tomogram; and a display means for displaying lines indicating the detected boundaries of the layers by superimposing them on the tomogram.

25. A non-transitory computer-readable storage medium storing a computer program causing an image processing apparatus to perform a method for processing an image of a tomogram obtained by capturing an image of an eye to be examined by a tomography apparatus, said method comprising:

an identifying step for identifying an artifact region in the tomogram;

a first detection step for detecting, by a first method, boundaries of layers constituting a retina of the eye to be examined in a region other than the artifact region;

a second detection step for detecting, by a second method different from the first method based on an intensity of the artifact region, boundaries of layers constituting the retina of the eye to be examined in the artifact region of the tomogram; and a display step for displaying lines indicating the detected boundaries of the layers by superimposing them on the tomogram.

26. A method for processing an image of a tomogram obtained by capturing an image of an eye to be examined by a tomography apparatus, comprising:

a first detection step for detecting, by a first method, boundaries of layers constituting a retina of the eye to be examined in the tomogram based on respective intensities of the layers;

an identifying step for identifying a region where the boundary detected in said first detecting step is discontinuous;

a second detection step for detecting, by a second method different from the first method based on the respective intensities of the layers, boundaries of layers in the identified region based on an intensity of the identified region; and a display step for displaying lines indicating the detected boundaries of the layers by superimposing them on the tomogram.

* * * * *